US008378102B2

(12) United States Patent
Lundquist, Jr. et al.

(10) Patent No.: US 8,378,102 B2
(45) Date of Patent: *Feb. 19, 2013

(54) OXIME AND HYDROXYLAMINE SUBSTITUTED THIAZOLO[4,5-C] RING COMPOUNDS AND METHODS

(75) Inventors: Gregory D. Lundquist, Jr., Eagan, MN (US); Tushar A. Kshirsagar, Woodbury, MN (US); Philip D. Heppner, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 894 days.

This patent is subject to a terminal disclaimer.

(21) Appl. No.: 11/884,060

(22) PCT Filed: Feb. 8, 2006

(86) PCT No.: PCT/US2006/004159
§ 371 (c)(1),
(2), (4) Date: May 18, 2010

(87) PCT Pub. No.: WO2007/120121
PCT Pub. Date: Oct. 25, 2007

(65) Prior Publication Data
US 2010/0240693 A1 Sep. 23, 2010

Related U.S. Application Data

(60) Provisional application No. 60/651,845, filed on Feb. 9, 2005.

(51) Int. Cl.
*C07D 513/14* (2006.01)
*A61K 31/4365* (2006.01)

(52) U.S. Cl. .......................................... 546/82; 514/293

(58) Field of Classification Search .................... 546/82; 514/293
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,904,669 A | 2/1990 | Knoll et al. |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |

(Continued)

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/003064 | 1/2005 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Silverman, R.B. The Organic Chemistry of Drug Design and Drug Action 1992, Academic: New York, p. 19.*

(Continued)

*Primary Examiner* — David K O'Dell

(57) ABSTRACT

Thiazolo[4,5-c]ring compounds, (e.g. thiazolopyridine, thiazoloquinoline, 6,7,8,9-tetrahydrothiazoloquinoline, thiazolonaphthyridine, and 6,7,8,9-tetrahydrothiazolonaphthyridine compounds) having an oxime or hydroxylamine substituent at the 2-position, pharmaceutical compositions containing the compounds, intermediates, and methods of making and methods of use of these compounds as immunomodulators, for modulating cytokine biosynthesis in animals and in the treatment of diseases including viral and neoplastic diseases are disclosed.

32 Claims, No Drawings

U.S. PATENT DOCUMENTS

| | | | |
|---|---|---|---|
| 6,610,319 B2 | 8/2003 | Tomai et al. | |
| 6,627,638 B2 | 9/2003 | Gerster et al. | |
| 6,627,640 B2 | 9/2003 | Gerster et al. | |
| 6,630,588 B2 | 10/2003 | Rice et al. | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,334 B2 * | 1/2004 | Gerster et al. | 514/232.8 |
| 6,677,347 B2 | 1/2004 | Crooks et al. | |
| 6,677,348 B2 | 1/2004 | Heppner et al. | |
| 6,677,349 B1 | 1/2004 | Griesgraber | |
| 6,683,088 B2 | 1/2004 | Crooks et al. | |
| 6,696,076 B2 | 2/2004 | Tomai et al. | |
| 6,696,465 B2 | 2/2004 | Dellaria et al. | |
| 6,703,402 B2 | 3/2004 | Gerster et al. | |
| 6,706,728 B2 | 3/2004 | Hedenstrom et al. | |
| 6,716,988 B2 | 4/2004 | Dellaria et al. | |
| 6,720,333 B2 | 4/2004 | Dellaria et al. | |
| 6,720,334 B2 | 4/2004 | Dellaria et al. | |
| 6,720,422 B2 | 4/2004 | Dellaria et al. | |
| 6,743,920 B2 | 6/2004 | Lindstrom et al. | |
| 6,756,382 B2 | 6/2004 | Coleman et al. | |
| 6,797,718 B2 | 9/2004 | Dellaria et al. | |
| 6,800,624 B2 | 10/2004 | Crooks et al. | |
| 6,809,203 B2 | 10/2004 | Gerster et al. | |
| 6,818,650 B2 | 11/2004 | Griesgraber | |
| 6,825,350 B2 | 11/2004 | Crooks et al. | |
| 6,841,678 B2 | 1/2005 | Merli et al. | |
| 6,852,861 B2 | 2/2005 | Merli et al. | |
| 6,878,719 B2 | 4/2005 | Lindstrom et al. | |
| 6,888,000 B2 | 5/2005 | Crooks et al. | |
| 6,894,060 B2 | 5/2005 | Slade | |
| 6,897,221 B2 | 5/2005 | Crooks et al. | |
| 6,903,113 B2 | 6/2005 | Heppner et al. | |
| 6,916,925 B1 | 7/2005 | Rice et al. | |
| 6,921,826 B2 | 7/2005 | Dellaria et al. | |
| 6,924,293 B2 | 8/2005 | Lindstrom | |
| 6,943,225 B2 | 9/2005 | Lee et al. | |
| 6,949,649 B2 | 9/2005 | Bonk et al. | |
| 6,953,804 B2 | 10/2005 | Dellaria et al. | |
| 6,969,722 B2 | 11/2005 | Heppner et al. | |
| 6,989,389 B2 | 1/2006 | Heppner et al. | |
| 7,030,129 B2 | 4/2006 | Miller et al. | |
| 7,030,131 B2 | 4/2006 | Crooks et al. | |
| 7,038,053 B2 | 5/2006 | Lindstrom et al. | |
| 7,049,439 B2 | 5/2006 | Crooks et al. | |
| 7,078,523 B2 | 7/2006 | Crooks et al. | |
| 7,091,214 B2 | 8/2006 | Hays et al. | |
| 7,098,221 B2 | 8/2006 | Heppner et al. | |
| 7,112,677 B2 | 9/2006 | Griesgraber | |
| 7,115,622 B2 | 10/2006 | Crooks et al. | |
| 7,125,890 B2 | 10/2006 | Dellaria et al. | |
| 7,132,429 B2 | 11/2006 | Griesgraber et al. | |
| 7,132,438 B2 | 11/2006 | Frenkel et al. | |
| 7,148,232 B2 | 12/2006 | Gerster et al. | |
| 7,157,453 B2 | 1/2007 | Crooks et al. | |
| 7,163,947 B2 | 1/2007 | Griesgraber et al. | |
| 7,179,253 B2 | 2/2007 | Graham et al. | |
| 7,199,131 B2 | 4/2007 | Lindstrom | |
| 7,214,675 B2 | 5/2007 | Griesgraber | |
| 7,220,758 B2 | 5/2007 | Dellaria et al. | |
| 7,226,928 B2 | 6/2007 | Mitra et al. | |
| 7,276,515 B2 | 10/2007 | Dellaria et al. | |
| 7,288,550 B2 | 10/2007 | Dellaria et al. | |
| 7,301,027 B2 | 11/2007 | Colombo et al. | |
| 7,375,180 B2 | 5/2008 | Gorden et al. | |
| 7,387,271 B2 | 6/2008 | Noelle et al. | |
| 7,393,859 B2 | 7/2008 | Coleman et al. | |
| 7,427,629 B2 | 9/2008 | Kedl et al. | |
| 7,485,432 B2 | 2/2009 | Fink et al. | |
| 7,544,697 B2 | 6/2009 | Hays et al. | |
| 7,576,068 B2 | 8/2009 | Averett | |
| 7,578,170 B2 | 8/2009 | Mayer et al. | |
| 7,579,359 B2 | 8/2009 | Krepski et al. | |
| 7,598,382 B2 | 10/2009 | Hays et al. | |
| 7,612,083 B2 | 11/2009 | Griesgraber | |
| 7,648,997 B2 | 1/2010 | Kshirsagar et al. | |
| 7,655,672 B2 | 2/2010 | Statham et al. | |
| 7,687,628 B2 | 3/2010 | Gutman et al. | |
| 7,696,159 B2 | 4/2010 | Owens et al. | |
| 7,699,057 B2 | 4/2010 | Miller et al. | |
| 7,731,967 B2 | 6/2010 | O'Hagan et al. | |
| 7,799,800 B2 | 9/2010 | Wightman | |
| 7,879,849 B2 | 2/2011 | Hays et al. | |
| 7,884,207 B2 | 2/2011 | Stoermer et al. | |
| 7,888,349 B2 | 2/2011 | Kshirsagar et al. | |
| 7,897,597 B2 | 3/2011 | Lindstrom et al. | |
| 7,897,609 B2 | 3/2011 | Niwas et al. | |
| 7,897,767 B2 | 3/2011 | Kshirsagar et al. | |
| 7,902,209 B2 | 3/2011 | Statham et al. | |
| 7,902,210 B2 | 3/2011 | Statham et al. | |
| 7,902,211 B2 | 3/2011 | Statham et al. | |
| 7,902,212 B2 | 3/2011 | Statham et al. | |
| 7,902,213 B2 | 3/2011 | Statham et al. | |
| 7,902,214 B2 | 3/2011 | Statham et al. | |
| 7,902,215 B2 | 3/2011 | Statham et al. | |
| 7,902,216 B2 | 3/2011 | Statham et al. | |
| 7,902,242 B2 | 3/2011 | Statham et al. | |
| 7,902,243 B2 | 3/2011 | Statham et al. | |
| 7,902,244 B2 | 3/2011 | Statham et al. | |
| 7,902,245 B2 | 3/2011 | Statham et al. | |
| 7,902,246 B2 | 3/2011 | Statham et al. | |
| 7,968,562 B2 | 6/2011 | Skwierczynski et al. | |
| 7,968,563 B2 | 6/2011 | Kshirsagar et al. | |
| 7,993,659 B2 | 8/2011 | Noelle et al. | |
| 8,017,779 B2 | 9/2011 | Merrill et al. | |
| 8,026,366 B2 | 9/2011 | Prince et al. | |
| 2002/0055517 A1 | 5/2002 | Smith | |
| 2002/0058674 A1 | 5/2002 | Hedenstrom et al. | |
| 2002/0107262 A1 | 8/2002 | Lindstrom | |
| 2003/0133913 A1 | 7/2003 | Tomai et al. | |
| 2003/0139364 A1 | 7/2003 | Krieg et al. | |
| 2004/0014779 A1 | 1/2004 | Gorden et al. | |
| 2004/0132079 A1 | 7/2004 | Gupta et al. | |
| 2004/0175336 A1 | 9/2004 | Egging et al. | |
| 2004/0180919 A1 | 9/2004 | Lee et al. | |
| 2004/0191833 A1 | 9/2004 | Fink et al. | |
| 2004/0197865 A1 | 10/2004 | Gupta et al. | |
| 2004/0202720 A1 | 10/2004 | Wightman et al. | |
| 2004/0214851 A1 | 10/2004 | Birmachu et al. | |
| 2004/0258698 A1 | 12/2004 | Wightman et al. | |
| 2004/0265351 A1 | 12/2004 | Miller et al. | |
| 2005/0048072 A1 | 3/2005 | Kedl et al. | |
| 2005/0059072 A1 | 3/2005 | Birmachu et al. | |
| 2005/0070460 A1 | 3/2005 | Hammerbeck et al. | |
| 2005/0096259 A1 | 5/2005 | Tomai et al. | |
| 2005/0106300 A1 | 5/2005 | Chen et al. | |
| 2005/0158325 A1 | 7/2005 | Hammerbeck et al. | |
| 2005/0165043 A1 | 7/2005 | Miller et al. | |
| 2005/0171072 A1 | 8/2005 | Tomai et al. | |
| 2005/0239735 A1 | 10/2005 | Miller et al. | |
| 2005/0245562 A1 | 11/2005 | Garcia-Echeverria et al. | |
| 2006/0045885 A1 | 3/2006 | Kedl et al. | |
| 2006/0045886 A1 | 3/2006 | Kedl | |
| 2006/0051374 A1 | 3/2006 | Miller et al. | |
| 2006/0088542 A1 | 4/2006 | Braun | |
| 2006/0142202 A1 | 6/2006 | Alkan et al. | |
| 2006/0142235 A1 | 6/2006 | Miller et al. | |
| 2006/0195067 A1 | 8/2006 | Wolter et al. | |
| 2006/0216333 A1 | 9/2006 | Miller et al. | |
| 2007/0060754 A1 | 3/2007 | Lindstrom et al. | |
| 2007/0066639 A1 | 3/2007 | Kshirsagar et al. | |
| 2007/0072893 A1 | 3/2007 | Krepski et al. | |
| 2007/0099901 A1 | 5/2007 | Krepski et al. | |
| 2007/0123559 A1 | 5/2007 | Statham et al. | |
| 2007/0155767 A1 | 7/2007 | Radmer et al. | |
| 2007/0166384 A1 | 7/2007 | Zarraga et al. | |
| 2007/0167479 A1 | 7/2007 | Busch et al. | |
| 2007/0213355 A1 | 9/2007 | Capraro et al. | |
| 2007/0219196 A1 | 9/2007 | Krepski et al. | |
| 2007/0243215 A1 | 10/2007 | Miller et al. | |
| 2007/0259881 A1 | 11/2007 | Dellaria et al. | |

| | | |
|---|---|---|
| 2007/0259907 A1 | 11/2007 | Prince |
| 2007/0287725 A1 | 12/2007 | Moser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 1983(1):78-82.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings,", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Deleopment of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

* cited by examiner

OXIME AND HYDROXYLAMINE SUBSTITUTED THIAZOLO[4,5-C] RING COMPOUNDS AND METHODS

CROSS REFERENCE TO RELATED APPLICATIONS

The present invention claims priority to U.S. Provisional Application Ser. No. 60/651,845, filed Feb. 9, 2005, which is incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a new class of compounds that are useful in inducing cytokine biosynthesis in animals. Such compounds are of the following Formula I:

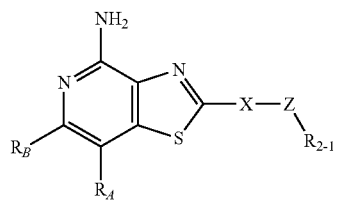

I wherein $R_A$, $R_B$, X, Z, and $R_{2-1}$ are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection or disease and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I, II, and III:

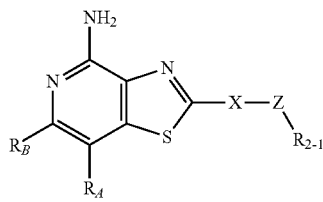

I

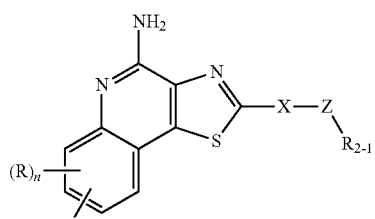

II

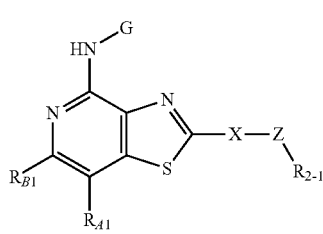

III as well as intermediates of the following Formulas X and XI:

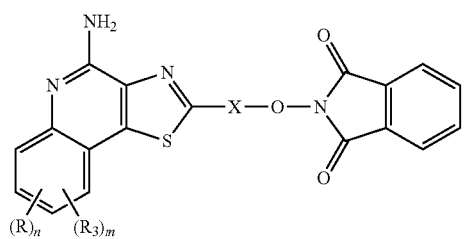

X

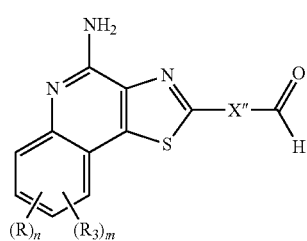

XI wherein $R_A$, $R_B$, $R_{A1}$, $R_{B1}$, R, $R_{2-1}$, $R_3$, G, n, m, X, X", and Z are as defined below, and pharmaceutically acceptable salts thereof.

In one embodiment, the present invention provides a compound of Formula I:

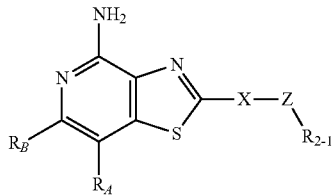

wherein:
Z is selected from the group consisting of:
—O—N=C($R_{2-2}$)—,
—C(=N—O—$R_{2-3}$)—,
—O—N($R_{2-4}$)—Y—, and
—C($R_{2-6}$)(—N(—O$R_{2-3}$)—Y—$R_{2-5}$)—;

X is selected from the group consisting of $C_{1-4}$ alkylene and $C_{3-4}$ alkenylene; with the proviso that X can also be a bond when Z is —C(=N—O$R_{2-3}$)— or —C($R_{2-6}$)(—N(—O$R_{2-3}$)—Y—$R_{2-5}$)—;

$R_{2-1}$, $R_{2-2}$, $R_{2-3}$, $R_{2-4}$, and $R_{2-6}$ are independently selected from the group consisting of:
  hydrogen,
  alkyl,
  alkenyl,
  aryl,
  arylalkylenyl,
  heteroaryl,
  heteroarylalkylenyl,
  heterocyclyl,
  heterocyclylalkylenyl, and
  alkyl, alkenyl, aryl, arylalkylenyl, heteroaryl, heteroarylalkylenyl, heterocyclyl, or heterocyclylalkylenyl, substituted by one or more substituents selected from the group consisting of:
    hydroxy,
    alkyl,
    haloalkyl,
    hydroxyalkyl,
    alkoxy,
    dialkylamino,
    —S(O)$_{0-2}$—$R_{2-7}$,
    —NH—S(O)$_2$—$R_{2-7}$,
    haloalkoxy,
    halogen,
    cyano,
    nitro,
    —$N_3$,
    aryl,
    heteroaryl,
    heterocyclyl,
    aryloxy,
    arylalkyleneoxy,
    —C(O)—O-alkyl,
    —C(O)—N($R_8$)$_2$,
    —N($R_8$)—C(O)—$R_{2-7}$,
    —NH—C(O)—NH—$R_{2-7}$,
    —NH—C(O)—NH$_2$,
    —O—(CO)-alkyl, and
    —C(O)-alkyl;

with the proviso that $R_{2-3}$ is other than alkenyl wherein the carbon atom bonded to —O— is doubly bonded to another carbon atom;

or $R_{2-1}$ and $R_{2-2}$ can join together to form a ring system selected from the group consisting of:

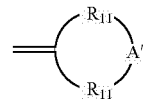

wherein the total number of atoms in the ring is 4 to 9, and

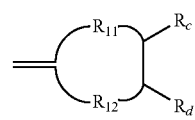

wherein the total number of atoms in the ring is 4 to 9;

or $R_{2-1}$ and $R_{2-4}$ together with the Y group and the nitrogen atom to which they are bonded can join to form a ring selected from the group consisting of:

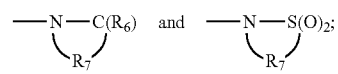

$R_{2-6}$ is selected from the group consisting of hydrogen, $C_{1-4}$alkyl, and phenyl;

$R_{2-7}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —$N_3$;

Y is selected from the group consisting of:
a bond,
—C($R_6$)—,
—S(O)$_2$—,
—S(O)$_2$—N($R_8$)—,

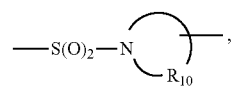

—C(O)—O—,
—C($R_6$)—N($R_8$)—,
—C(O)—N($R_8$)S(O)$_2$—,
—C($R_6$)—N($R_8$)—C(O)—,

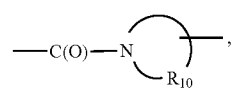

—C(O)—C(O)—,
—C(O)—C(O)—O—, and
—C(=NH)—N($R_8$)—;

$R_A$ and $R_B$ are each independently selected from the group consisting of:
hydrogen,
halogen,
alkyl,
alkenyl,
alkoxy,
alkylthio, and
—$N(R_9)_2$;
or when taken together, $R_A$ and $R_B$ form a fused benzene ring or fused pyridine ring wherein the a fused benzene ring or fused pyridine ring is unsubstituted or substituted by one or more R''' groups;
or when taken together, $R_A$ and $R_B$ form a fused cyclohexene ring or a fused tetrahydropyridine ring, wherein the fused cyclohexene or tetrahydropyridine ring is unsubstituted or substituted by one or more R groups;
R is selected from the group consisting of:
halogen,
hydroxy,
alkyl,
alkenyl,
haloalkyl,
alkoxy,
alkylthio, and
—$N(R_9)_2$;
R''' is a non-interfering substituent;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;
$R_9$ is selected from the group consisting of hydrogen and alkyl;
$R_{10}$ is $C_{3-8}$ alkylene;
$R_{11}$ is $C_{1-6}$ alkylene or $C_{2-6}$ alkenylene, wherein the alkylene or alkenylene is optionally interrupted by one heteroatom;
$R_{12}$ is selected from the group consisting of a bond, $C_{1-5}$ alkylene, and $C_{2-5}$ alkenylene, wherein the alkylene or alkenylene is optionally interrupted by one heteroatom;
$R_c$ and $R_d$ are independently selected from the group consisting of hydrogen, halogen, hydroxy, alkyl, alkenyl, aryl, haloalkyl, alkoxy, alkylthio, and —$N(R_9)_2$; or $R_c$ and $R_d$ can join to form a fused aryl ring or fused 5-10 membered heteroaryl ring containing one to four heteroatoms;
A' is selected from the group consisting of —O—, —$S(O)_{0-2}$—, —$N(-Q-R_4)$—, and —$CH_2$—;
Q is selected from the group consisting of a bond, —$C(R_6)$—, —$C(R_6)$—$C(R_6)$—, —$S(O)_2$—, —$C(R_6)$—N$(R_8)$—W—, —$S(O)_2$—$N(R_8)$—, —$C(R_6)$—O—, —$C(R_6)$—S—, and —$C(R_6)$—$N(OR_9)$—; and
W is selected from the group consisting of a bond, —C(O)—, and —$S(O)_2$—;
or a pharmaceutically acceptable salt thereof.

In another embodiment, the present invention provides a compound of Formula II:

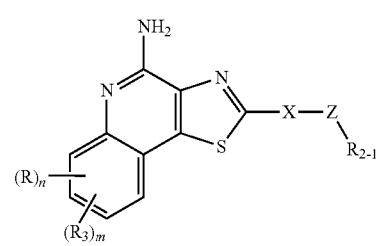

wherein:
Z is selected from the group consisting of:
—O—N=C($R_{2-2}$)—,
—C(=N—O—$R_{2-3}$)—,
—O—N($R_{2-4}$)—Y—, and
—C($R_{2-6}$)(—N(—$OR_{2-3}$)—Y—$R_{2-5}$)—;
X is selected from the group consisting of $C_{1-4}$ alkylene and $C_{3-4}$ alkenylene; with the proviso that X can also be a bond when Z is —C(=N—O—$R_{2-3}$)— or —C($R_{2-6}$)(—N(—$OR_{2-3}$)—Y—$R_{2-5}$)—;
$R_{2-1}$, $R_{2-2}$, $R_{2-3}$, $R_{2-4}$, and $R_{2-5}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—$S(O)_{0-2}$—$R_{2-7}$,
—NH—$S(O)_2$—$R_{2-7}$,
haloalkoxy,
halogen,
cyano,
nitro,
—$N_3$,
aryl,
heteroaryl,
heterocyclyl,
aryloxy,
arylalkyleneoxy,
—C(O)—O-alkyl,
—C(O)—$N(R_8)_2$,
—$N(R_8)$—C(O)—$R_{2-7}$,
—NH—C(O)—NH—$R_{2-7}$, —NH—C(O)—NH$_2$,
—O—(CO)-alkyl, and
—C(O)-alkyl;
with the proviso that R$_{2-3}$ is other than alkenyl wherein the carbon atom bonded to —O— is doubly bonded to another carbon atom;
or R$_{2-1}$ and R$_{2-2}$ can join together to form a ring system selected from the group consisting of:

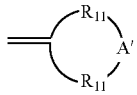

wherein the total number of atoms in the ring is 4 to 9, and

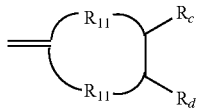

wherein the total number of atoms in the ring is 4 to 9;
or R$_{2-1}$ and R$_{2-4}$ together with the Y group and the nitrogen atom to which they are bonded can join to form a ring selected from the group consisting of:

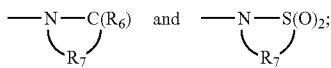

R$_{2-6}$ is selected from the group consisting of hydrogen, C$_{1-4}$alkyl, and phenyl;
R$_{2-7}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N3;
Y is selected from the group consisting of:
a bond,
—C(R$_6$)—,
—S(O)$_2$—,
—S(O)$_2$N(R$_8$)—,

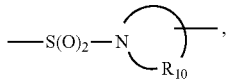

—C(O)—O—,
—C(R$_6$)—N(R$_8$)—,
—C(CO)—N(R$_8$)—S(O)$_2$—,
—C(R$_6$)—N(R$_8$)—C(O)—,

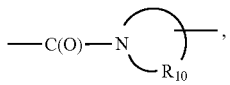

—C(O)—C(O)—,
—C(O)—C(O)—O—, and
—C(=NH)—N(R$_8$)—;

R is selected from the group consisting of:
halogen,
hydroxy,
alkyl,
alkenyl,
haloalkyl,
alkoxy,
alkylthio, and
—N(R$_9$)$_2$;
R$_3$ is selected from the group consisting of:
—Z'—R$_4$,
—Z'—X'—R$_4$,
—Z'—X'—Y'—R$_4$,
—Z'—X'—Y'—X'—Y'—R$_4$, and
—Z'—X'—R$_5$;
n is an integer from 0 to 4;
m is 0 or 1; with the proviso that when m is 1, then n is 0 or 1;
X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;
Y' is selected from the group consisting of:
—O—,
—S(O)$_{0-2}$—,
—S(O)$_2$N(R$_8$)—,
—C(R$_6$)—,
—C(R$_6$)—O—,
—O—C(R$_6$)—,
—O—C(O)—O—,
—N(R$_8$-Q-,
—C(R$_8$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

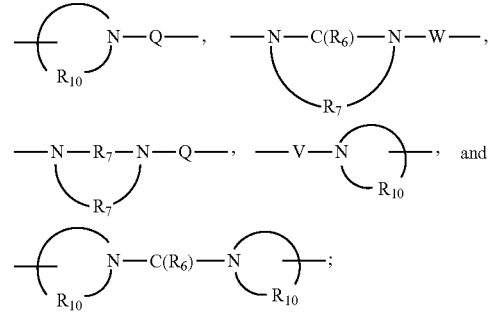

Z' is a bond or —O—;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

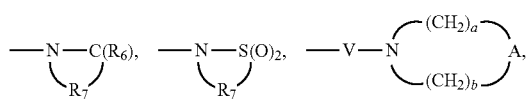

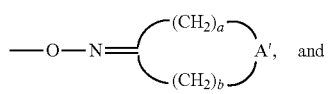  and

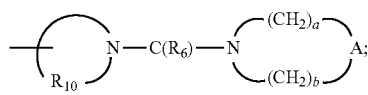

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

$R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

A is selected from the group consisting of —O—, —C(O)—, —S(O)$_{0-2}$—, —CH$_2$—, and —N(-Q-R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In another embodiment, the present invention provides a compound of Formula III:

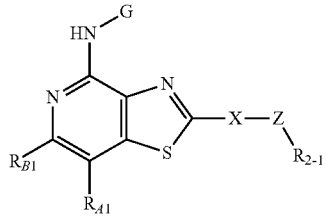

III wherein:
G is selected from the group consisting of:
—C(O)—R',
α-aminoacyl,
α-aminoacyl-α-aminoacyl,
—C(O)—O—R',
—C(O)—N(R")R',
—C(=NY$_1$)—R',
—CH(OH)—C(O)—OY$_1$,
—CH(OC$_{1-4}$ alkyl)Y$_0$,
—CH$_2$Y$_2$, and
—CH(CH$_3$)Y$_2$;

R' and R" are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an α-amino acid selected from the group consisting of racemic, D-, and L-amino acids;

$Y_1$ is selected from the group consisting of hydrogen, $C_{1-6}$ alkyl, and benzyl;

$Y_0$ is selected from the group consisting of $C_{1-6}$ alkyl, carboxy-$C_{1-6}$ alkylenyl, amino-$C_{1-4}$ alkylenyl, mono-N—$C_{1-5}$ alkylamino-$C_{1-4}$ alkylenyl, and di-N,N—$C_{1-4}$ alkylamino-$C_{1-4}$ alkylenyl;

$Y_2$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl;

$R_{A1}$ and $R_{B1}$ are each independently selected from the group consisting of:
hydrogen,
halogen,
alkyl,
alkenyl,
alkoxy,
alkylthio, and
—N(R$_9$)$_2$;

or when taken together, $R_{A1}$ and $R_{B1}$ form a fused benzene ring or fused pyridine ring wherein the a fused benzene ring or fused pyridine ring is unsubstituted or substituted by one $R_3$ group, or one $R_3$ group and one R group, or one, two, three, or four R groups when on the fused benzene ring, or one, two, or three R groups when on the fused pyridine ring;

or when taken together, $R_{A1}$ and $R_{B1}$ form a fused cyclohexene ring or a fused tetrahydropyridine ring, wherein the fused cyclohexene or tetrahydropyridine ring is unsubstituted or substituted by one or more R groups; and R, R$_3$, R$_9$, X, Z, and R$_{2-1}$ are defined as in Formula II above; or a pharmaceutically acceptable salt thereof.

In one embodiment, the present invention provides an intermediate compound of Formula X:

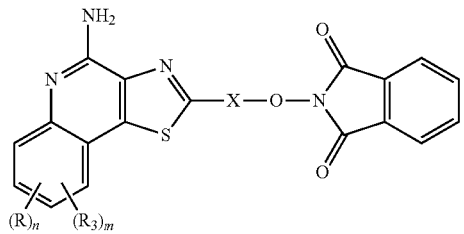

wherein:

X is selected from the group consisting of C$_{1-4}$ alkylene and C$_{2-4}$ alkenylene; and R, R$_3$, n, and m are defined as in Formula II above;

or a pharmaceutically acceptable salt thereof.

In another embodiment, the present invention provides an intermediate compound of Formula XI:

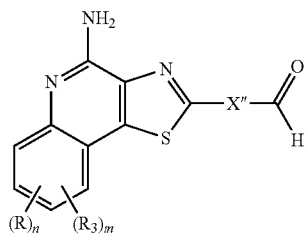

wherein:

X" is selected from the group consisting of a bond, C$_{1-4}$ alkylene, and C$_{2-4}$ alkenylene; and R, R$_3$, n, and m are defined as in Formula II above; or a pharmaceutically acceptable salt thereof.

Herein, "non-interfering" means that the ability of the compound or salt, which includes a non-interfering substituent to modulate the biosynthesis of one or more cytokines is not destroyed by the non-interfering substituent. For certain embodiments, R''' is a non-interfering substituent. Illustrative non-interfering R''' groups include those described above for R and R$_3$.

As used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl(azepanyl), 1,4-oxazepanyl, homopiperazinyl(diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —C(O)—N(R$_8$)$_2$ each R$_8$ group is independently selected. In another example, when an R$_{2-1}$ and an R$_{2-2}$ group both contain an R$_{2-7}$ group, each R$_{2-7}$ group is independently selected. In a further example, when more than one Y' group is present and each Y' group contains one or more R$_8$ groups, then each Y' group is independently selected, and each R$_8$ group is independently selected.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or ail of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Z, X, Y, Y', R$_A$, R$_B$, R, R$_{2-1}$, R$_3$, Q, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formula I, R''' is a non-interfering substituent

For certain embodiments of Formula I, the one or more R''' groups are one R$_3$ group, or one R$_3$ group and one R group, or one, two, three, or four R groups when on the fused benzene ring, or one, two, or three R groups when on the fused pyridine ring.

For certain embodiments of Formula I or III, R$_A$ and R$_B$ or R$_{A1}$ and R$_{B1}$, respectively, are each independently selected from the group consisting of hydrogen, halogen, alkyl, alkenyl, alkoxy, alkylthio, and —N(R$_9$)$_2$. For certain embodiments, R$_A$ and R$_B$ or R$_{A1}$ and R$_{B1}$ are each independently selected from the group consisting of hydrogen and alkyl. For certain embodiments, R$_A$ and R$_B$ or R$_{A1}$ and R$_{B1}$ are both methyl.

For certain embodiments of Formula I, R$_A$ and R$_B$ are taken together to form a fused benzene ring wherein the benzene ring is unsubstituted or substituted by one or more R''' groups. In certain of these embodiments, the fused benzene ring is substituted by one or two R''' groups. In certain of these embodiments, the one or two R''' groups are one R$_3$ group, or one R$_3$ group and one R group. In certain of these embodiments, the fused benzene ring is unsubstituted.

For certain embodiments of Formula I, R$_A$ and R$_B$ are taken together to form a fused pyridine ring wherein the pyridine ring is unsubstituted or substituted by one or more R''' groups.

In certain of these embodiments, the fused pyridine ring is substituted by one or two R''' groups. In certain of these embodiments, the one or two R''' groups are one R$_3$ group, or one R$_3$ group and one R group. In certain of these embodiments, the fused pyridine ring is

wherein the highlighted bond is the position where the ring is fused. In certain of these embodiments, the fused pyridine ring is unsubstituted.

For certain embodiments of Formula III, R$_{A1}$ and R$_{B1}$ are taken together to form a fused benzene ring wherein the benzene ring is unsubstituted or substituted by one R$_3$ group, or one R$_3$ group and one R group. In certain of these embodiments, the fused benzene ring is unsubstituted.

For certain embodiments of Formula III, R$_{A1}$ and R$_{B1}$ are taken together to form a fused pyridine ring wherein the pyridine ring is unsubstituted or substituted by one R$_3$ group, or one R$_3$ group and one R group. In certain of these embodiments, the fused pyridine ring is

wherein the highlighted bond is the position where the ring is fused. In certain of these embodiments, the fused pyridine ring is unsubstituted.

For certain embodiments of Formula I or III, R$_A$ and R$_B$ or R$_{A1}$ and R$_{B1}$, respectively, are taken together to form a fused cyclohexene ring wherein the fused cyclohexene ring is unsubstituted or substituted by one or more R groups. The double bond in the cyclohexene ring is the position where the ring is fused. In certain of these embodiments, the fused cyclohexene ring is unsubstituted.

For certain embodiments of Formula I or III, R$_A$ and R$_B$ or R$_{A1}$ and R$_{B1}$, respectively, are taken together to form a fused tetrahydropyridine ring, wherein the fused tetrahydropyridine ring is unsubstituted or substituted by one or more R groups. The double bond in the tetrahydropyridine ring is the position where the ring is fused. In certain of these embodiments, the tetrahydropyridine ring is

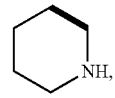

wherein the highlighted bond indicates the position where the ring is fused. In certain of these embodiments, the fused tetrahydropyridine ring is unsubstituted.

For certain embodiments, including any one of the above embodiments of Formulas I, II, or III where R can be present, R is selected from the group consisting of halogen, hydroxy, alkyl, alkenyl, haloalkyl, alkoxy, alkylthio, and —N(R$_9$)$_2$. For certain of these embodiments, R is selected from the group consisting of alkyl, alkoxy, hydroxy, halogen, and trifluoromethyl. For certain of these embodiments, R is halogen or hydroxy. For certain of these embodiments R is hydroxy.

Alternatively, for certain of these embodiments, R is halogen. For certain of these embodiments R is bromine.

For certain embodiments, including any one of the above embodiments where R can be present, R is not present.

For certain of embodiments, including any one of the above embodiments where $R_3$ can be present $R_3$ is not present.

For certain embodiments of Formula II, n is 0.

For certain embodiments, including any one of the above embodiments of Formula II, m is 0.

For certain embodiments, including any one of the above embodiments where $R_3$ is present $R_3$ is selected from the group consisting of —Z'—$R_4$, —Z'—X'—$R_4$, —Z'—X'—Y'—$R_4$, —Z'—X'—Y'—X'—Y'—$R_4$, and —Z'—X'—$R_5$.

For certain embodiments, including any one of the above embodiments where $R_3$ is present $R_3$ is selected from the group consisting of —Z'—$R_4$, —Z'—X'—Y'—$R_4$, and —Z'—X'—$R_5$.

For certain embodiments, including any one of the above embodiments where $R_3$ is present $R_3$ is selected from the group consisting of phenyl, pyridin-3-yl, pyridin-4-yl, 5-(hydroxymethyl)pyridin-3-yl, 2-ethoxyphenyl, 3-(morpholine-4-carbonyl)phenyl, and 3-(N,N-dimethylaminocarbonyl)phenyl.

For certain embodiments, $R_3$ is —Z'—$R_4$. For certain of these embodiments, $R_3$ is selected from the group consisting of phenyl, pyridin-3-yl, pyridin-4-yl, 5-(hydroxymethyl)pyridin-3-yl, and 2-ethoxyphenyl. For certain of these embodiments, $R_3$ is phenyl.

For certain embodiments, $R_3$ is —Z'—X'—Y'—$R_4$. For certain of these embodiments, $R_3$ is selected from the group consisting of 3-(methylsulfonylamino)phenyl, 3-(morpholine-4-carbonyl)phenyl, and 3-(N,N-dimethylaminocarbonyl)phenyl.

For certain embodiments, including any one of the above embodiments, Z is —O—N=C($R_{2-2}$)—. For certain of these embodiments, $R_{2-1}$ and $R_{2-2}$ join together to form a ring system selected from the group consisting of:

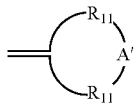

wherein the total number of atoms in the ring is 4 to 9, and

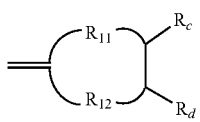

wherein the total number of atoms in the ring is 4 to 9. For certain of these embodiments, $R_{2-1}$ and $R_{2-2}$ join together to form the ring:

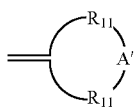

wherein the total number of atoms in the ring is 4 to 9. For certain of these embodiments, $R_{2-1}$ and $R_{2-2}$ join together to form the ring:

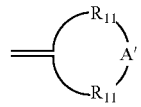

wherein $R_{11}$ is —(CH$_2$)$_{1-2}$—, and A' is —CH$_2$— or —N(-Q-$R_4$)— wherein Q is a bond or —C(O)—, and $R_4$ is alkyl For certain of these embodiments, the ring is

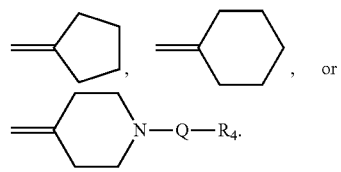

Alternatively, for certain of these embodiments where $R_{2-1}$ and $R_{2-2}$ join together to form a ring system, $R_{2-1}$ and $R_{2-2}$ join together to form the ring system:

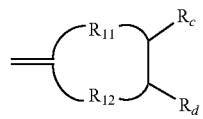

wherein the total number of atoms in the ring is 4 to 9. For certain of these embodiments, $R_c$ and $R_d$ are independently selected from the group consisting of hydrogen, halogen, hydroxy, alkyl, alkenyl, aryl, haloalkyl, alkoxy, alkylthio, and —N($R_9$)$_2$. Alternatively, for certain of these embodiments, $R_c$ and $R_d$ can join to form a fused aryl ring or fused 5-10 membered heteroaryl ring containing one to four heteroatoms. For certain of these embodiments, the fused aryl ring is a benzene ring.

Alternatively, for certain of these embodiments where Z is —O—N=C($R_{2-2}$)—, at least one of $R_{2-1}$ or $R_{2-2}$ is selected from the group consisting of alkyl, alkenyl, aryl, arylalkylenyl, heteroaryl, heteroarylalkylenyl, heterocyclyl, and heterocyclylalkylenyl, each of which is unsubstituted or substituted by one or more substituents selected from the group consisting of hydroxy, alkyl, haloalkyl, hydroxy alkyl, alkoxy, dialkylamino, —S(O)$_{0-2}$—$R_{2-7}$, —NH—S(O)$_2$—$R_{2-7}$, haloalkoxy, halogen, cyano, nitro, aryl, heteroaryl, heterocyclyl, aryloxy, arylalkyleneoxy, —C(O)—O-alkyl, —C(O)—N($R_8$)$_2$, —N($R_8$)—C(O)—$R_{2-7}$, —N(H)—C(O)—NH—$R_{2-7}$, —O—(CO)-alkyl, and —C(O)-alkyl. For certain of these embodiments, at least one of $R_{2-1}$ or $R_{2-2}$ is selected from the group consisting of alkyl, aryl, arylalkylenyl, heteroaryl, and heterocyclyl, each of which is unsubstituted or substituted by one or more substituents selected from the group consisting of hydroxy, alkyl, alkoxy, halogen, cyano, and —C(O)—O-alkyl. For certain of these embodiments, one of $R_{2-1}$ or $R_{2-2}$ is hydrogen. Alternatively, for certain of these embodiments, $R_{2-1}$ and $R_{2-2}$ are independently $C_{1-10}$ alkyl. For certain of these embodiments, $R_{2-1}$ and $R_{2-2}$ are each methyl.

For certain embodiments, including any one of the above embodiments except where Z is —O—N=C($R_{2-2}$)—, Z is —O—N($R_{2-4}$)—Y—. For certain of these embodiments, $R_{2-4}$ is hydrogen. For certain of these embodiments, Y is selected from the group consisting of —C(O)—, —S(O)$_2$—, —S(O)$_2$—N($R_8$)—, —C(O)—O—, and —C(O)—N($R_8$)—.

For certain of these embodiments, $R_{2-1}$ is selected from the group consisting of alkyl, aryl, arylalkylenyl, heteroaryl, and heterocyclyl, each of which is unsubstituted or substituted with one or more substituents selected from the group consisting of alkyl, alkoxy, and halogen.

For certain embodiments, including any one of the above embodiments except where Z is —O—N=C($R_{2-2}$)— or —ON($R_{2-4}$)—Y—, Z is —C(=N—O—$R_{2-3}$)—. For certain of these embodiments, $R_{2-3}$ is selected from the group consisting of hydrogen, alkyl, arylalkylenyl, and heteroarylalkylenyl. For certain of these embodiments, $R_{2-3}$ is hydrogen, $C_{1-4}$ alkyl, benzyl, or pyridin-2-ylmethyl. For certain of these embodiments, $R_{2-1}$ is selected from the group consisting of hydrogen, alkyl, and aryl. For certain of these embodiments, $R_{2-1}$ is hydrogen, $C_{1-4}$ alkyl, or phenyl. For certain of these embodiments, $R_{2-1}$ is hydrogen.

For certain embodiments, including any one of the above embodiments except where Z is —O—N=C($R_{2-2}$)—, —O—N($R_{2-4}$)—Y—, or —C(=N—O—$R_{2-3}$)—, Z is —C($R_{2-6}$)(—N(—O$R_{2-3}$)—Y—$R_{2-5}$)—. For certain of these embodiments, $R_{2-6}$ is hydrogen. For certain of these embodiments, $R_{2-3}$ is selected from the group consisting of hydrogen, alkyl, arylalkylenyl, and heteroarylalkylenyl. For certain of these embodiments, $R_{2-3}$ is hydrogen, $C_{1-4}$ alkyl, benzyl, or pyridin-2-ylmethyl. For certain of these embodiments, $R_{2-5}$ is hydrogen or $C_{1-4}$ alkyl. For certain of these embodiments, $R_{2-5}$ is hydrogen or methyl, and Y is a bond. For certain of these embodiments, $R_{2-1}$ is selected from the group consisting of hydrogen, alkyl, and aryl. For certain of these embodiments, $R_{2-1}$ is hydrogen, $C_{1-4}$ alkyl, or phenyl.

For certain embodiments, including any one of the above embodiments, X is selected from the group consisting of $C_{1-4}$ alkylene and $C_{3-4}$ alkenylene; with the proviso that X can also be a bond when Z is —C(=N—O—$R_{2-3}$)— or —C($R_{2-6}$)(—N(—O$R_{2-3}$)—Y—$R_{2-5}$)—. For certain of these embodiments, X is $C_{1-4}$ alkylene. For certain of these embodiments, X is methylene.

For certain embodiments, including any one of the above embodiments not excluding this definition, X is a bond.

For certain embodiments, including any of the above embodiments where $R_3$ is present, —$R_3$ is at the 7-position.

For certain embodiments, $R_{2-1}$, $R_{2-2}$, $R_{2-3}$, $R_{2-4}$, and $R_{2-5}$ are independently selected from the group consisting of hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of hydroxy, alkyl, haloalkyl, hydroxyalkyl, alkoxy, dialkylamino, —S(O)$_{0-2}$—$R_{2-7}$, —NH—S(O)$_2$—$R_{2-7}$, haloalkoxy, halogen, cyano, nitro, —N$_3$, aryl, heteroaryl, heterocyclyl, aryloxy, arylalkyleneoxy, —C(O)—O-alkyl, —C(O)—N($R_8$)$_2$, —N($R_8$)—C(O)—$R_{2-7}$, —NH—C(O)—NH—$R_{2-7}$, —NH—C(O)—NH$_2$, —O—(CO)-alkyl, and —C(O)-alkyl; with the proviso that $R_{2-3}$ is other than alkenyl wherein the carbon atom bonded to —O— is doubly bonded to another carbon atom;

or $R_{2-1}$ and $R_{2-2}$ can join together to form a ring system selected from the group consisting of:

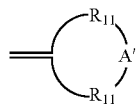

wherein the total number of atoms in the ring is 4 to 9, and

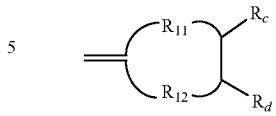

wherein the total number of atoms in the ring is 4 to 9;

or $R_{2-1}$ and $R_{2-4}$ together with the Y group and the nitrogen atom to which they are bonded can join to form a ring selected from the group consisting of:

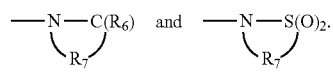

For certain embodiments, $R_{2-1}$ is selected from the group consisting of alkyl, alkenyl, aryl, arylalkylenyl, heteroaryl, heteroarylalkylenyl, heterocyclyl, and heterocyclylalkylenyl, each of which is unsubstituted or substituted by one or more substituents selected from the group consisting of hydroxy, alkyl, haloalkyl, hydroxyalkyl, alkoxy, dialkylamino, —S(O)$_{0-2}$—$R_{2-7}$, —NH—S(O)$_2$—$R_{2-7}$, haloalkoxy, halogen, cyano, nitro, aryl, heteroaryl, heterocyclyl, aryloxy, arylalkyleneoxy, —C(O)—O-alkyl, —C(O)—N($R_8$)$_2$, —N($R_8$)—C(O)—$R_{2-7}$, —N(H)—C(O)—NH—$R_{2-7}$, —O—(CO)-alkyl, and —C(O)-alkyl.

For certain embodiments, $R_{2-1}$ is selected from the group consisting of alkyl, aryl, arylalkylenyl, heteroaryl, and heterocyclyl, each of which is unsubstituted or substituted by one or more substituents selected from the group consisting of hydroxy, alkyl, alkoxy, halogen, cyano, and —C(O)—O-alkyl.

For certain embodiments, $R_{2-1}$ is selected from the group consisting of alkyl, aryl, arylalkylenyl, heteroaryl, and heterocyclyl, each of which is unsubstituted or substituted with one or more substituents selected from the group consisting of alkyl, alkoxy, and halogen.

For certain embodiments, $R_{2-1}$ is selected from the group consisting of hydrogen, alkyl, and aryl.

For certain embodiments, $R_{2-1}$ is hydrogen, $C_{1-4}$ alkyl, or phenyl.

For certain embodiments, $R_{2-1}$ is $C_{1-10}$ alkyl.

For certain embodiments, $R_{2-1}$ is methyl.

For certain embodiments, $R_{2-1}$ is hydrogen.

For certain embodiments, $R_{2-2}$ is selected from the group consisting of alkyl, alkenyl, aryl, arylalkylenyl, heteroaryl, heteroarylalkylenyl, heterocyclyl, and heterocyclylalkylenyl, each of which is unsubstituted or substituted by one or more substituents selected from the group consisting of hydroxy, alkyl, haloalkyl, hydroxyalkyl, alkoxy, dialkylamino, —S(O)$_{0-2}$—$R_{2-7}$, —NH—S(O)$_2$—$R_{2-7}$, haloalkoxy, halogen, cyano, nitro, aryl, heteroaryl, heterocyclyl, aryloxy, arylalkyleneoxy, —C(O)—O-alkyl, —C(O)—N($R_8$)$_2$, —N($R_8$)—C(O)—$R_{2-7}$, —N(H)—C(O)—NH—$R_{2-7}$, —O—(CO)-alkyl, and —C(O)-alkyl.

For certain embodiments, $R_{2-2}$ is selected from the group consisting of alkyl, aryl, arylalkylenyl, heteroaryl, and heterocyclyl, each of which is unsubstituted or substituted by one or more substituents selected from the group consisting of hydroxy, alkyl, alkoxy, halogen, cyano, and —C(O)—O-alkyl.

For certain embodiments, $R_{2-2}$ is hydroxy alkyl.

For certain embodiments, $R_{2-2}$ is hydroxymethyl.

For certain embodiments, $R_{2-2}$ is $C_{1-10}$ alkyl.
For certain embodiments, $R_{2-2}$ is methyl.
For certain embodiments, $R_{2-2}$ is hydrogen.
For certain embodiments, $R_{2-3}$ is selected from the group consisting of hydrogen, alkyl, arylalkylenyl, and heteroarylalkylenyl.
For certain embodiments, $R_{2-3}$ is hydrogen, $C_{1-4}$ alkyl, benzyl, or pyridin-2-ylmethyl.
For certain embodiments, $R_{2-4}$ is hydrogen.
For certain embodiments, $R_{2-5}$ is hydrogen or alkyl.
For certain embodiments, $R_{2-5}$ is hydrogen or $C_{1-4}$ alkyl.
For certain embodiments, $R_{2-6}$ is selected from the group consisting of hydrogen, $C_{1-4}$ alkyl, and phenyl.
For certain embodiments, $R_{2-6}$ is hydrogen.
For certain embodiments, $R_{2-7}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkyl thio, haloalkyl, haloalkoxy, alkyl, and —$N_3$.
For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.
For certain embodiments, $R_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, and aryl; whereto aryl and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents.
For certain embodiments, $R_4$ is aryl or heteroaryl, each of which is unsubstituted of substituted by hydroxyalkyl or alkoxy.
For certain embodiments, $R_4$ is hydrogen or alkyl.
For certain embodiments, $R_4$ is $C_{1-4}$ alkyl.
For certain embodiments, $R_5$ is selected from the group consisting of:

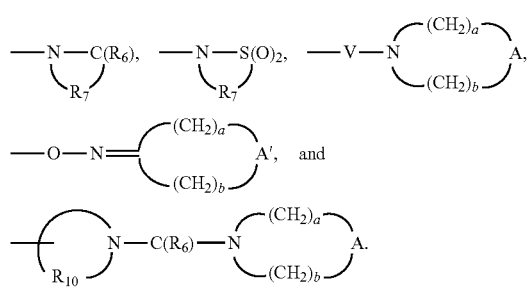

For certain embodiments, $R_5$ is selected from the groin) consisting of:

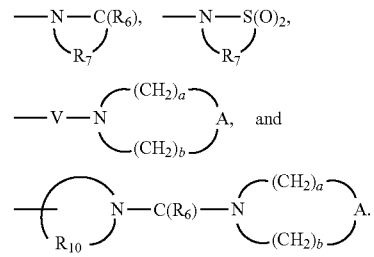

For certain embodiments, $R_5$ is selected from the group consisting of

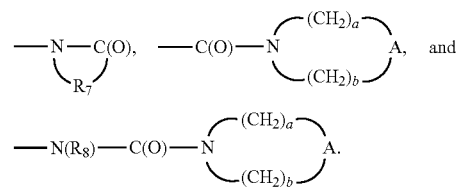

In certain of these embodiments A is —O—, —$CH_2$—, or —$S(O)_2$—; $R_7$ is $C_{2-4}$ alkylene; $R_8$ is hydrogen or $C_{1-4}$ alkyl; and a and b are each independently 1 to 3. In certain of these embodiments a and b are each 2.
For certain embodiments, $R_5$ is

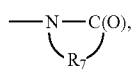

and $R_7$ is $C_{2-4}$ alkylene.
For certain embodiments, $R_6$ is selected from the group consisting of =O and =S.
For certain embodiments, $R_6$ is =O.
For certain embodiments, $R_7$ is $C_{2-7}$ alkylene.
For certain embodiments, $R_7$ is $C_{2-4}$ alkylene.
For certain embodiments, $R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl.
For certain embodiments, $R_8$ is selected from the group consisting of hydrogen, $C_{1-4}$ alkyl, and $C_{1-4}$ alkoxy$C_{1-4}$ alkylenyl.
For certain embodiments, $R_8$ is hydrogen or $C_{1-4}$ alkyl.
For certain embodiments, $R_8$ is hydrogen.
For certain embodiments, $R_9$ is selected from the group consisting of hydrogen and alkyl.
For certain embodiments, $R_{10}$ is $C_{3-8}$ alkylene.
For certain embodiments, $R_{10}$ is $C_{4-6}$ alkylene.
For certain embodiments, $R_{11}$ is $C_{1-6}$ alkylene or $C_{2-6}$ alkenylene, wherein the alkylene or alkenylene is optionally interrupted by one heteroatom.
For certain embodiments, $R_{11}$ is methylene or ethylene.
For certain embodiments, $R_{12}$ is selected from the group consisting of a bond, $C_{1-5}$ alkylene, and $C_{2-5}$ alkenylene, wherein the alkylene or alkenylene is optionally interrupted by one heteroatom.

For certain embodiments, $R_{12}$ is methylene or ethylene.

For certain embodiments, $R_c$ and $R_d$ are independently selected from the group consisting of hydrogen, halogen, hydroxy, alkyl, alkenyl, aryl, haloalkyl, alkoxy, alkylthio, and —N($R_9$)$_2$.

For certain embodiments, $R_c$ and $R_d$ can join to form a fused aryl ring or fused 5-10 membered heteroaryl ring containing one to four heteroatoms.

For certain embodiments, A is selected from the group consisting of —O—, —C(O)—, —S(O)$_{0-2}$—, —CH$_2$—, and —N(-Q-R$_4$)—.

For certain embodiments, A is —O—, —CH$_2$—, or —S(O)$_2$—.

For certain embodiments, A is —O— or —S(O)$_2$—.

For certain embodiments, A is —O—.

For certain embodiments, A' is selected from the group consisting of —O—, —S(O)$_{0-2}$—, —N(-Q-R$_4$)—, and —CH$_2$—.

In certain embodiments, A' is selected from the group consisting of —CH$_2$—, —S(O)$_2$—, and —O—.

In certain embodiments, A' is —N(-Q-R$_4$)—.

In certain embodiments, A' is —CH$_2$—.

In certain embodiments, A' is —O—.

For certain embodiments, including any one of the above embodiments of Formula III, G is selected from the group consisting of —C(O)—R', α-aminoacyl, α-aminoacyl-α-aminoacyl, —C(O)—O—R', —C(O)—N(R")R', —C(=NY$_1$)—R', —CH(OH)—C(O)—OY$_1$, —CH(OC$_{1-4}$ alkyl)Y$_0$, —CH$_2$Y$_2$, and —CH(CH$_3$)Y$_2$. For certain of these embodiments, R' and R" are independently selected from the group consisting of C$_{1-10}$ alkyl, C$_{3-7}$cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; α-aminoacyl is an α-aminoacyl group derived from an α-amino acid selected from the group consisting of racemic, D-, and L-amino acids; Y$_1$ is selected from the group consisting of hydrogen, C$_{1-6}$ alkyl, and benzyl; Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl; and Y$_2$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments of Formula III, G is selected from the group consisting of —C(O)—R', α-aminoacyl, and —C(O)—O—R'.

For certain embodiments, including any one of the above embodiments of Formula III, G is selected from the group consisting of —C(O)—R', α-amino-C$_{2-11}$ acyl, and —C(O)—O—R'. α-Amino-C$_{2-11}$ acyl includes α-amino acids containing a total of at least 2 carbon atoms and a total of up to 11 carbon atoms, and may also include one or more heteroatoms selected from the group consisting of O, S, and N. For certain of these embodiments, R' contains one to ten carbon atoms.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the α-amino acid is selected from the group consisting of racemic, D-, and L-amino acids.

In certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—.

In certain embodiments, Q is selected from the group consisting of a bond, —C(O)—, —S(O)$_2$—, and —C(R$_6$)—N(R$_8$)—.

In certain embodiments, Q is —C(O)—.

In certain embodiments, Q is a bond.

In certain embodiments, V is selected from the group consisting of —C(R$_6$)—, —O—C(R$_6$)—, —N(R$_8$)—C(R$_6$)—, and —S(O)$_2$—.

In certain embodiments, V is selected from the group consisting of —C(O)— and —N(R$_8$)—C(O)—.

In certain embodiments, W is selected from the group consisting of a bond, —C(O)—, and —S(O)$_2$—.

In certain embodiments, W is a bond.

In certain embodiments, X is selected from the group consisting of C$_{1-4}$ alkylene and C$_{3-4}$ alkenylene; with the proviso that X can also be a bond when Z is —C(=N—O—R$_{2-3}$)— or —C(R$_{2-6}$)(—N(—OR$_{2-3}$)—Y—R$_{2-5}$)—.

In certain embodiments, X is C$_{1-4}$ alkylene.

In certain embodiments, X is methylene.

In certain embodiments, X is a bond. For example, X can be a bond when Z is —C(=N—O—R$_{2-3}$)— or —C(R$_{2-6}$)(—N(—OR$_{2-3}$)—Y—R$_{2-5}$)—.

In certain embodiments, X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups.

In certain embodiments, X' is arylene.

In certain embodiments, X' is phenylene.

In certain embodiments, X" is selected from the group consisting of a bond, C$_{1-4}$ alkylene, and C$_{2-4}$ alkenylene.

In certain embodiments, X" is C$_{1-4}$ alkylene.

In certain embodiments, Y is selected from the group consisting of a bond, —C(R$_6$)—, —S(O)$_2$—, —S(O)$_2$—N(R$_8$)—,

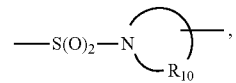

—C(O)—O—, —C(R$_6$)—N(R$_8$)—, —C(O)—N(R$_8$)—S(O)$_2$—, —C(R$_6$)—N(R$_8$)—C(O)—,

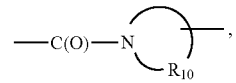

—C(O)—C(O)—, —C(O)—C(O)—O—, and —C(=NH)—N(R$_8$)—.

In certain embodiments, Y is selected from the group consisting of —C(O)—, —S(O)$_2$—, —S(O)$_2$N(R$_8$)—, —C(O)—O—, and —C(O)—N(R$_8$)—.

In certain embodiments, Y is a bond.

In certain embodiments, Y' is selected from the group consisting of —O—, —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—, —CH(—N(—O—R$_8$)-Q-R$_4$)—, $$\left(\begin{array}{c}\phantom{x}\\R_{10}\end{array}\right)N-Q-,\quad -N-C(R_6)-N-W-,$$
$$\phantom{xxxxxxxxxxxxxxxxxxxxxxxxxxxx}R_7$$

$$-N-R_7-N-Q-,\quad -V-N\left(\begin{array}{c}\phantom{x}\\R_{10}\end{array}\right)-,\text{ and}$$
$$\phantom{xx}R_7$$

$$\left(\begin{array}{c}\phantom{x}\\R_{10}\end{array}\right)N-C(R_6)-N\left(\begin{array}{c}\phantom{x}\\R_{10}\end{array}\right)-.$$

In certain embodiments, Y' is —C(O)—N(R$_8$)—.

In certain embodiments, Z' is a bond or —O—.

In certain embodiments, Z' is a bond.

In certain embodiments, Z' is —O—.

In certain embodiments, a and b are independently integers from 1 to 6 with the proviso that a+b is ≦7.

In certain embodiments, a and b are each independently 1 to 3.

In certain embodiments, a and b are each 2.

In certain embodiments, n is an integer form 0 to 4.

In certain embodiments, n is 0 or 1.

In certain embodiments, n is 0.

In certain embodiments, m is 0 or 1; with the proviso that when m is 1, then n is 0or 1.

In certain embodiments, m is 0.

In certain embodiments, m is 1.

For certain embodiments of Formula X or Formula XI, m is 0.

For certain embodiments of Formula X or Formula XI, R$_3$ is benzyloxy, and n is 0.

For certain embodiments, the present invention provides a pharmaceutical composition comprising a therapeutically effective amount of a compound or salt of any one of the above embodiments of Formulas I, II, and III, and a pharmaceutically acceptable carrier.

For certain embodiments, the present invention provides a method of inducing cytokine biosynthesis in an animal comprising administering an effective amount of a compound or salt of any one of the above embodiments of Formulas I, II, and III, or a pharmaceutical composition comprising an effective amount of a compound or salt of any one of the above embodiments of Formulas I, II, and III to the animal. For certain of these embodiments, the cytokine is selected from the group consisting of IFN-α, TNF-α, IL-6, IL-10, and IL-12. For certain of these embodiments, the cytokine is IFN-α or TNF-α. For certain of these embodiments, the cytokine is IFN-α.

For certain embodiments, the present invention provides a method of treating a viral disease in an animal comprising administering a therapeutically effective amount of a compound or salt of any one of the above embodiments of Formulas I, II, and III, or a pharmaceutical composition comprising a therapeutically effective amount of a compound or salt of any one of the above embodiments of Formulas I, II, and III to the animal.

For certain embodiments, the present invention provides a method of treating a neoplastic disease in an animal comprising administering a therapeutically effective amount of a compound or salt of any one of the above embodiments of Formulas I, II, and III, or a pharmaceutical composition comprising a therapeutically effective amount of a compound or salt of any one of the above embodiments of Formulas I, II, and III to the animal.

Preparation of the Compounds

Compounds of the invention may be synthesized by synthetic routes that include processes analogous to those well known in the chemical arts, particularly in light of the description contained herein. The starring materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, N.Y., (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate mat other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I, wherein R$_{2-1}$, R$_{2-2}$, R$_{2-4}$, and Y are as defined above; X is C$_{1-4}$ alkylene or C$_{3-4}$ alkenylene; P is a hydroxy protecting group; and $R_{A1}$ and $R_{B1}$ are each independently selected from the group consisting of hydrogen, halogen, alkyl, alkenyl, alkoxy, and —$N(R_9)_2$, or when taken together $R_{A1}$ and $R_{B1}$ form a fused benzene ring or pyridine ring wherein the benzene ring is optionally substituted by one, two, three, or four R groups, and the pyridine ring is optionally substituted by one, two, or three R groups, wherein R is as defined above.

In step (1) of Reaction Scheme I, a compound of Formula XV or a salt thereof is reacted with a carboxylic acid or an equivalent thereof to provide a compound of Formula XVI. Suitable equivalents to carboxylic acid include acid anhydrides of Formula O[C(O)—X—O—P]$_2$ and acid chlorides of Formula Cl—C(O)—X—O—P. The reaction is conveniently carried out by adding an acid chloride of Formula Cl—C(O)—X—O—P to a solution of a compound of Formula XV in a suitable solvent such as dichloromethane or acetonitrile in the presence of a tertiary amine such as triethylamine, pyridine, or 4-dimethylaminopyridine to afford an amide. The reaction can be carried out at or below room temperature. The amide product can be isolated and optionally purified using conventional techniques. Several compounds of Formula XV are known or can be prepared by known synthetic methods; known compounds include unsubstituted and substituted pyridines, quinolines, and naphthyridines of each isomeric variation. See, for example, U.S. Pat. No. 6,110,929 (Gerster et al) and the references cited therein. Some compounds of Formula Cl—C(O)—X—O—P, such as acetoxyacetyl chloride, methoxyacetyl chloride, and 2-methoxypropionyl chloride, are commercially available. Others can be prepared by known synthetic methods.

In step (2) of Reaction Scheme I, a compound of Formula XVI is reacted with phosphorus pentasulfide to provide a thiazole of Formula XVII. The reaction can be carried out by adding phosphorus pentasulfide to a solution or suspension of a compound of Formula XVI in a suitable solvent such as pyridine and heating the resulting mixture at an elevated temperature, such as the reflux temperature of the solvent. The product can be isolated and optionally purified using conventional techniques.

In step (3) of Reaction Scheme I, a compound of Formula XVII is oxidized to provide a 5N-oxide of Formula XVIII using a conventional oxidizing agent capable of forming N-oxides. The reaction is conveniently carried out by adding 3-chloroperoxybenzoic acid to a solution of a thiazole of Formula XVII in a solvent such as dichloromethane or chloroform. The reaction can be carried out at room temperature, and the product can be isolated using conventional methods.

In step (4) of Reaction Scheme I, a 5N-oxide of Formula XVIII is aminated to provide a compound of Formula XIX. Step (4) can be carried out by the reaction of a 5N-oxide of Formula XVIII with trichloroacetyl isocyanate followed by hydrolysis of the resulting intermediate to provide a compound of Formula XIX. The reaction is conveniently carried out in two steps by (i) adding trichloroacetyl isocyanate to a solution of the N-oxide of Formula XVIII in a solvent such as dichloromethane and stirring at room temperature to provide an isolable amide intermediate. In step (ii), a solution of the intermediate in a suitable solvent such as ethanol or methanol is treated with a base such as potassium ethoxide, sodium methoxide, or ammonium hydroxide at room temperature. The product or a pharmaceutically acceptable salt thereof can be isolated using conventional methods.

Alternatively, step (4) can be carried out by the activation of an N-oxide of Formula XVIII by conversion to an ester and then reacting the ester with an animating agent Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide followed by p-toluenesulfonyl chloride to a solution of the N-oxide of Formula XVIII in a suitable solvent such as chloroform or dichloromethane. The reaction may be carried out at room temperature, and the product or a pharmaceutically acceptable salt thereof may be isolated by conventional methods.

Steps (3) and (4) can alternatively be combined and carried out as a one-pot procedure by adding 3-chloroperoxybenzoic acid to a solution of a compound of Formula XVII in a solvent such as dichloromethane or chloroform and then adding ammonium hydroxide and p-toluenesulfonyl chloride without isolating the N-oxide of Formula XVIII. The product of Formula XIX or a pharmaceutically acceptable salt thereof can be isolated using conventional methods.

In step (5) of Reaction Scheme I, the protecting group of a thiazole of Formula XIX is removed to provide a hydroxyalkyl-substituted thiazole of Formula XX. The deprotection can be carried out using a variety of methods depending on which P group is present When P is —C(O)—CH$_3$, the reaction is conveniently carried out by adding lithium hydroxide monohydrate to a solution or suspension of the compound of Formula XIX in a suitable solvent or solvent system such as tetrahydrofuran:methanol:water. The reaction can be carried out at room temperature, and the product can be isolated by conventional methods.

In step (6) of Reaction Scheme I, the hydroxy group of a thiazole of Formula XX is converted to a chloro group using conventional methods. The reaction is conveniently carried out by adding thionyl chloride to a solution of the compound of Formula XX in a suitable solvent such as dichloromethane and then heating the reaction at an elevated temperature, such as the reflux temperature of the solvent The product of Formula XXI can be isolated by conventional methods.

In step (7) of Reaction Scheme I, the chloro group of a thiazole of Formula XXI is displaced with N-hydroxyphthalimide to provide an N-phthalimide-protected thiazole hydroxylamine of Formula XXII. The reaction is conveniently carried out by adding a base, such as triethylamine, to a solution of N-hydroxyphthalimide in a suitable solvent such as N,N-dimethylformamide (DMF); and then adding the chloro-substituted thiazole of Formula XXI, optionally in a suitable solvent such as DMF, to the resulting mixture. The reaction can be carried out at room temperature. The product or a pharmaceutically acceptable salt thereof can be isolated using conventional methods.

Alternatively, a hydroxy-substituted thiazole of Formula XX can be converted to an N-phthalimide-protected thiazole hydroxylamine of Formula XXII in one step as shown in step (6a) of Reaction Scheme I. In step (6a) a thiazole of Formula XX is treated with N-hydroxyphthalimide under Mitsunobu reaction conditions. The reaction is conveniently carried out by adding triphenylphosphine and N-hydroxyphthalimide to a solution or suspension of a compound of Formula XX in a suitable solvent such as tetrahydrofuran (THF) or DMF, and then slowly adding diethyl azodicarboxylate or diisopropyl azodicarboxylate. The reaction can be carried out at room temperature or at an elevated temperature, such as 60° C. The product or a pharmaceutically acceptable salt thereof can be isolated using conventional methods.

In step (8) of Reaction Scheme I, an N-phthalimide-protected thiazole hydroxylamine of Formula XXII is converted to a hydroxylamine of Formula XXIII, a subgenus of Formula I. Removal of the N-phthalimide protecting group is conveniently carried out by adding hydrazine or hydrazine hydrate to a suspension of a thiazole of Formula XXII in a suitable solvent such as ethanol. The reaction can be carried out at room temperature or at an elevated temperature such as the reflux temperature of the solvent The product or a pharmaceutically acceptable salt thereof can be isolated using conventional methods.

In step (9) of Reaction Scheme I, a hydroxylamine of Formula XXIII is reacted with an aldehyde or ketone of Formula $R_{2-1}C(O)R_{2-2}$ to provide an oxime of Formula XXIV, which is a subgenus of Formula I. Numerous aldehydes and ketones of Formula $R_{2-1}C(O)R_{2-2}$ are commercially available; others can be readily prepared using known synthetic methods. The reaction can be conveniently carried out by adding the aldehyde or ketone of Formula $R_{2-1}C(O)R_{2-2}$ to a hydroxylamine of Formula XXIII in a suitable solvent such as methanol. The reaction can be carried out at room temperature. The product or a pharmaceutically acceptable salt thereof can be isolated using conventional methods.

In step (10) of Reaction Scheme I, an oxime of Formula XXIV is reduced to provide a hydroxylamine of Formula XXV, which is a subgenus of Formula I, wherein Y is a bond. The reduction is conveniently carried out by treating an oxime of Formula XXIV with excess sodium cyanoborohydride in a suitable solvent or solvent mixture such as methanol/acetic acid. The reaction can be carried out at ambient temperature. The product or a pharmaceutically acceptable salt thereof can be isolated using conventional methods.

A hydroxylamine of Formula XXIII can also be treated according to step (9a) of Reaction Scheme I to provide compound of Formula XXVI, which is a subgenus of Formula I. Step (9a) is carried out using conventional methods. For example, sulfonamides of Formula XXVI (Y is —S(O)$_2$—) can be prepared by reacting a compound of Formula XXIII with a sulfonyl chloride of formula $R_{2-1}S(O)_2Cl$ or a sulfonic anhydride of Formula $[R_{2-1}S(O)_2]_2O$. The reaction can be carried out at room temperature in an inert solvent such as chloroform, dichloromethane, or N,N-dimethylacetamide (DMA) by adding the sulfonyl chloride or sulfonic anhydride to a compound of Formula XXIII in the presence of a base such as N,N-diisopropylethylamine, triethylamine, or pyridine.

Sulfamides of Formula XXVI (Y is —S(O)$_2$—N(R$_8$)— or

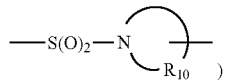

can be prepared by reacting a compound of Formula XXIII with sulfuryl chloride to generate a sulfamoyl chloride in situ, and then reacting the sulfamoyl chloride with an amine of formula HN(R$_8$)R$_{2-1}$, or

or by reacting a compound of Formula XXIII with a sulfamoyl chloride of formula $R_{2-1}(R_8)NS(O)_2Cl$ or

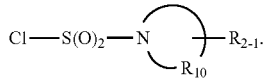

The product or a pharmaceutically acceptable salt thereof can be isolated using conventional methods. Many sulfonyl chlorides of formula $R_{2-1}S(O)_2Cl$, amines of formulas HN(R$_8$)R$_2$, and

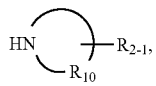

and some sulfamoyl chlorides of formulas $R_{2-1}(R_8)NS(O)_2Cl$ and

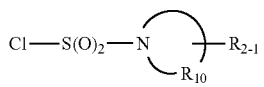

are commercially available; others can be prepared using known synthetic methods.

Amides of Formula XXVI (Y is —C(O)—) can be prepared from hydroxylamines of Formula XXIII using conventional methods. For example, a compound of Formula XXIII can be reacted with an acid chloride of formula $R_{2-1}C(O)Cl$. The reaction can be carried out by adding the acid chloride to a solution of a compound of Formula XXIII in a suitable solvent such as chloroform or DMA, optionally in the presence of a base such as N,N-diisopropylethylamine, triethylamine, or pyridine, at ambient temperature. The product or a pharmaceutically acceptable salt thereof can be isolated using conventional methods.

Ureas and thioureas of Formula XXVI (Y is —C(O)—N(R$_8$)—, —C(S)—N(R$_8$)—, —C(O)—N(R$_8$)—S(O)$_2$—, —C(O)—N(R$_8$)—C(O)—, —C(S)—N(R$_8$)—C(O)—, or

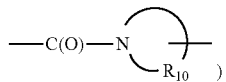

can be prepared from hydroxylamines of Formula XXIII using conventional methods. For example, a compound of Formula XXIII can be reacted with an isocyanate of formula $R_{2-1}N\!\!=\!\!C\!\!=\!\!O$. The reaction can be carried out by adding the isocyanate to a solution of a compound of Formula XXIII in a suitable solvent such as chloroform or DMA, optionally in the presence of a base such as N,N-diisopropylethylamine, or triethylamine, at room temperature. Alternatively, a compound of Formula XXIII can be reacted with a thioisocyanate of formula $R_{2-1}N\!\!=\!\!C\!\!=\!\!S$, a sulfonyl isocyanate of formula $R_{2-1}S(O)_2N\!\!=\!\!C\!\!=\!\!O$ or a carbamoyl chloride of formula $R_{2-1}NC(O)Cl$ or

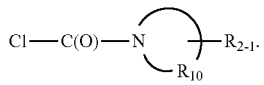

The product or a pharmaceutically acceptable salt thereof can be isolated using conventional methods.

The methods described in step (9a) can also be used to convert a hydroxylamine of Formula XXV to a compound of Formula XXVII, wherein $R_{2-4}$ is other than hydrogen, aryl, or heteroaryl, in step (11) of Reaction Scheme I. The product of Formula XXVII, a subgenus of Formula I, or a pharmaceutically acceptable salt thereof can be isolated using conventional methods.

A compound of Formula XXVI, wherein Y is $—C(R_6)—$, $—S(O)_2—$, or $—C(O)—C(O)—$, or a compound of Formula XXV, can be derivatized further upon treatment with an alkylating agent that is generated in situ from an alcohol of Formula $R_{2-4}—OH$ under Mitsunobu reaction conditions (described in step (6a) above) or an alkylating agent of Formula $R_{2-4}—Br$ or $R_{2-4}—I$ in the presence of a base such as cesium carbonate in a suitable solvent such as DMF. The latter reaction may be carried out at room temperature for reactive alkylating agents such as, for example, methyl iodide, benzyl bromide, and substituted benzyl bromides, or at an elevated temperature. Optionally, catalytic tetrabutylammonium hydrogensulfate can be added. One skilled in the art would recognize that the reactions described for the alkylation step would probably not be successful for $R_{2-4}$ groups that are difficult to introduce via bimolecular nucleophilic substitution reactions. These groups include, for example, sterically hindered alkyl groups. The product of Formula XXVII, a subgenus of Formula I, or a pharmaceutically acceptable salt thereof, can be isolated by conventional methods.

A compound of Formula XXVII in which $R_{2-1}$ and $R_{2-4}$ together with the nitrogen atom and Y group to which they are bonded join together to form a ring of Formula

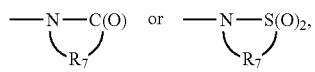

can be prepared in a two-step procedure from a compound of Formula XXIII by reaction with a chloroalkanoyl chloride of formula $Cl—R_7—C(O)Cl$ or a chloroalkanesulfonyl chloride of formula $Cl—R_7—S(O)_2Cl$, respectively. The reaction is preferably carried out by adding the chloroalkanoyl chloride or chloroalkanesulfonyl chloride to a solution of a compound of Formula XXIII in a suitable solvent such as dichloromethane in the presence of a base such as triethylamine. The intermediate chloroalkanamide or chloroalkanesulfonamide may optionally be isolated before treatment with a stronger base such as 1,8-diazabicyclo[5.4.0]undecene-7 (DBU) at ambient temperature. If the intermediate chloroalkanamide or chloroalkanesulfonamide is isolated, the reaction with DBU can be carried out in a suitable solvent such as DMF. The product or a pharmaceutically acceptable salt thereof can be isolated using conventional methods. Alternatively, a reagent of the Formula $P—O—R_7—C(O)Cl$, wherein P is a protecting group, may react with a compound of Formula XXIII to generate an isolable intermediate that can then be deprotected to yield a hydroxyalkanamide. The hydroxyalkanamide is then cyclized under Mitsunobu conditions, described in step (6a) above to provide a compound of Formula XXVII in which $R_{2-1}$ and $R_{2-4}$ together with the nitrogen atom and Y group to which they are bonded join together to form a ring of Formula

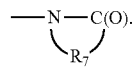

The product or a pharmaceutically acceptable salt thereof can be isolated using conventional methods.

Reaction Scheme I

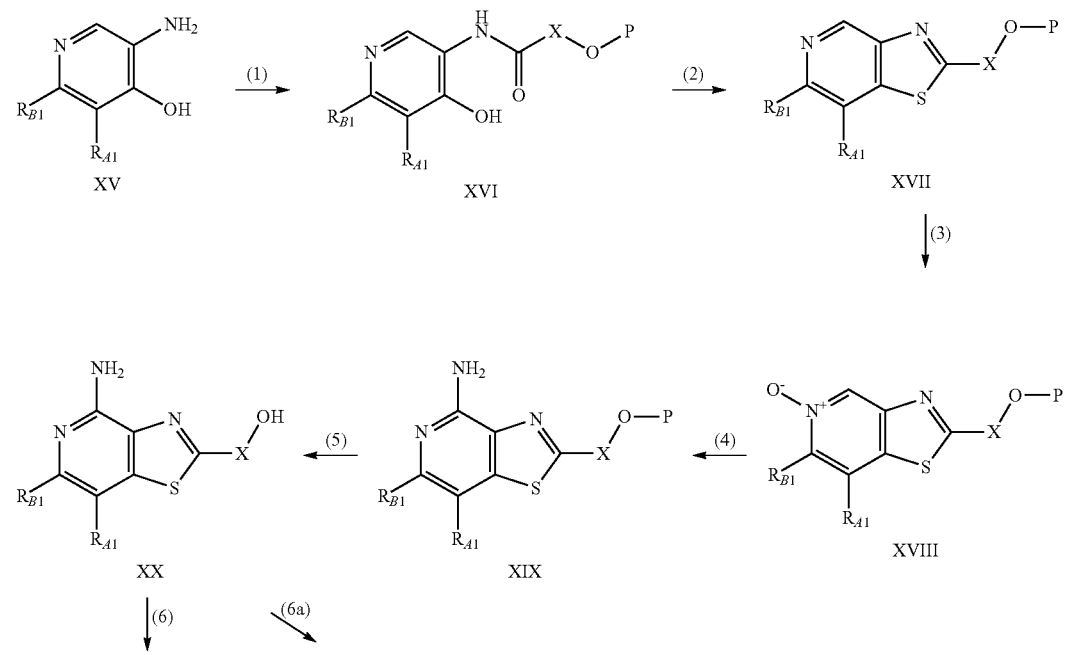

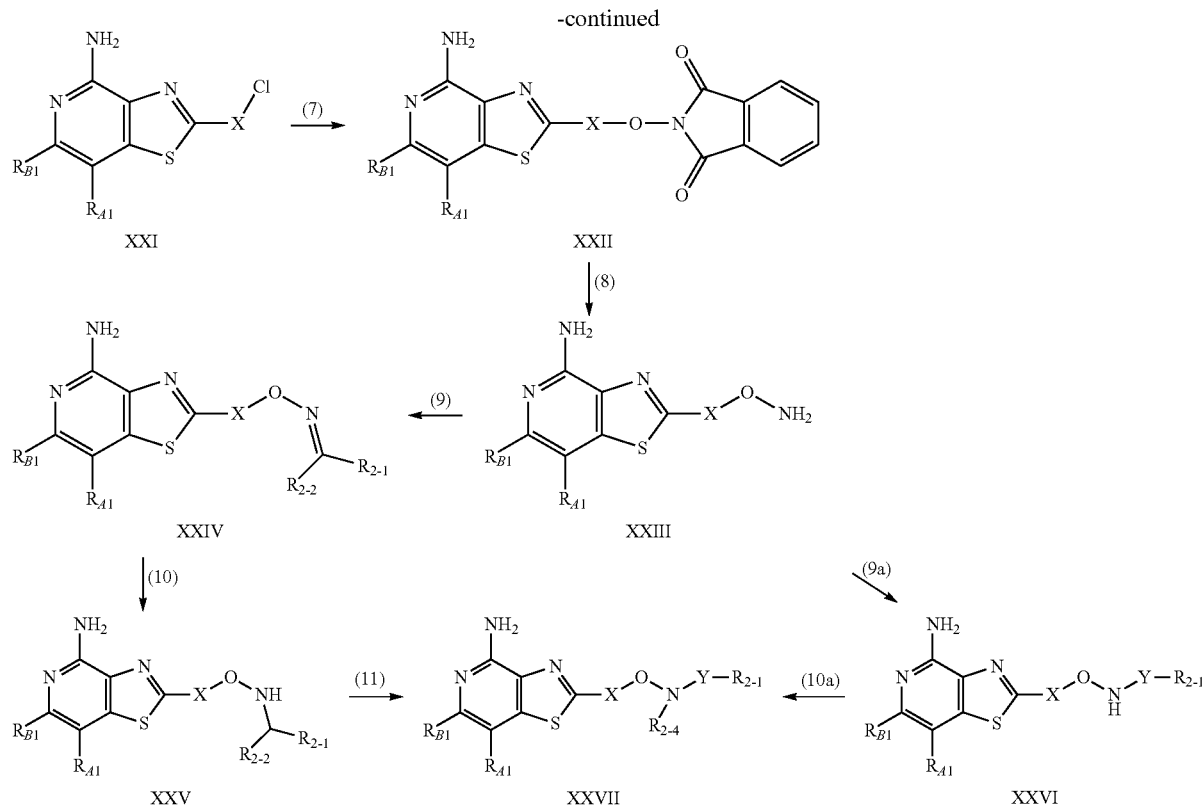

Compounds of the invention can be prepared according to Reaction Scheme II, wherein $R_{A1}$, $R_{B1}$, $R_{2-1}$, $R_{2-3}$, and $R_{2-5}$ are as defined above, and $X_a$ is selected from the group consisting of a bond, $C_{1-4}$ alkylene, and $C_{3-4}$ alkenylene. In step (1) of Reaction Scheme II, the protecting group of a thiazole of Formula XVIIa is removed to provide a hydroxyalkyl-substituted thiazole of Formula XXVIII. The reaction can be carried out as described in step (5) of Reaction Scheme I, and the product can be isolated by conventional methods.

In step (2) of Reaction Scheme II, a hydroxyalkyl-substituted thiazole of Formula XXVIII is oxidized to an aldehyde-substituted thiazole of Formula XXIX using one of many conventional methods. The oxidation is conveniently carried out by adding Dess-Martin periodinane, [1,1,1-tris(acetyloxy)-1,1-dihydro-1,2-benziodoxol-3(1H)-one], to a solution or suspension of a hydroxyalkyl-substituted thiazole of Formula XXVIII in a suitable solvent such as dichloromethane. The reaction can be carried out at room temperature, and the product can be isolated by conventional methods.

In step (3) of Reaction Scheme II, an aldehyde-substituted thiazole of Formula XXIX is converted to an aldoxime of Formula XXX. The reaction is conveniently carried out by adding a hydroxylamine salt of the formula $NH_2OR_{2-3}$·HCl, optionally in a suitable solvent such as water, to a solution or suspension of a compound of Formula XXIX, in a suitable solvent, such as ethanol or methanol. Optionally a base such as aqueous sodium hydroxide can be added. The reaction can be carried out at room temperature or at an elevated temperature such as the reflux temperature of the solvent Hydroxylamine salts of the formula $NH_2OR_{2-3}$·HCl can be obtained commercially or they can be prepared using conventional synthetic methods. The product or a pharmaceutically acceptable salt thereof is obtained as a mixture of E and Z isomers and can be isolated using conventional methods.

In steps (4) and (S) of Reaction Scheme II, an aldoxime-substituted thiazole of Formula XXX is first oxidized to an N-oxide of Formula XXXI, which is then aminated to provide a compound of Formula XXXII, which is a subgenus of Formula I. Steps (4) and (5) of Reaction Scheme II can be carried out according to the methods described in steps (3) and (4) of Reaction Scheme I, and the product or a pharmaceutically acceptable salt thereof can be isolated by conventional methods.

In step (6) of Reaction Scheme II, an aldoxime-substituted thiazole of Formula XXXII is treated with a Grignard reagent of the formula $R_{2-1}$MgHalide to form a hydroxylamine of Formula XXXIII, a subgenus of Formula I. Several Grignard reagents are commercially available; others can be prepared using known synthetic methods. The reaction is conveniently carried out by adding a solution of two equivalents of the Grignard reagent to a solution of the compound of Formula XXXII in a suitable solvent such as THF. The reaction can be carried out at room temperature, and the product can be isolated using conventional methods. Alternatively, to prepare a compound of Formula XXXIII wherein $R_{2-1}$ is hydrogen, an oxime of Formula XXXII can be treated with a hydride reducing agent for example, under the conditions described in step (10) of Reaction Scheme I.

In step (7) of Reaction Scheme II, a hydroxylamine of Formula XXXIII is converted to a compound of Formula XXXIV using one of the methods described in step (9a) of Reaction Scheme I. The product of Formula XXXIV, a subgenus of Formula I, or a pharmaceutically acceptable salt thereof can be isolated by conventional methods.

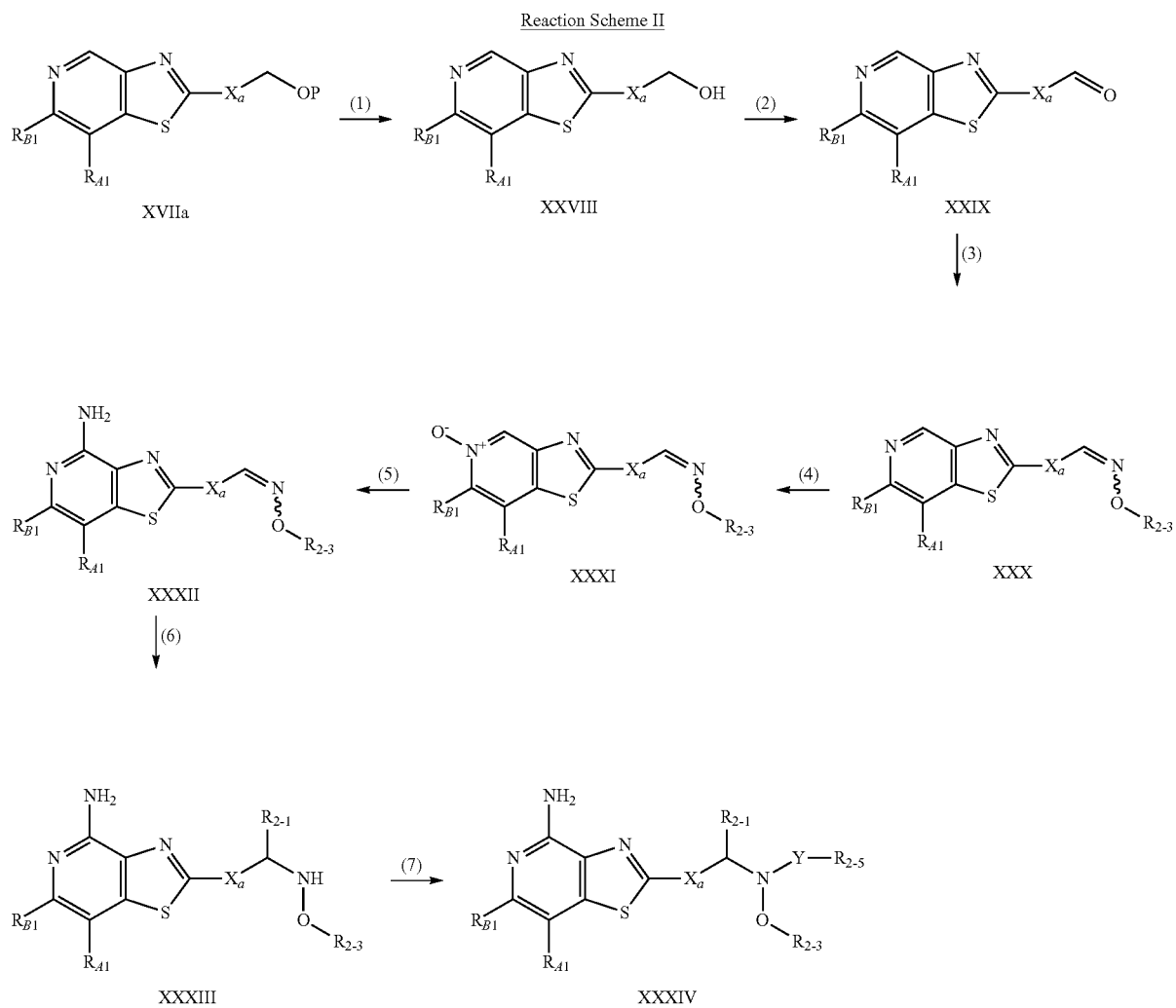

Reaction Scheme II

Compounds of the invention can be prepared according to Reaction Scheme III, wherein $R_{A1}$, $R_{B1}$, $R_{2-1}$, $R_{2-3}$, $R_{2-5}$, $R_{2-6}$, and $X_a$ are as defined above. In step (1) of Reaction Scheme III, an aldehyde-substituted thiazole of Formula XXIX is treated with a Grignard reagent of the formula $R_{2-1}$MgHalide to form a secondary alcohol of Formula XXXV. Several Grignard reagents are commercially available; others can be prepared using known synthetic methods. The reaction is conveniently carried out by adding a solution of the Grignard reagent to a solution of the compound of Formula XXIX in a suitable solvent such as THF. The reaction can be carried out at room temperature, and the product can be isolated using conventional methods.

In step (2) of Reaction Scheme III, an alcohol-substituted thiazole of Formula XXXV is oxidized to a ketone-substituted thiazole of Formula XXXVI using conventional methods. The reaction is conveniently carried out using Dess-Martin periodinane under the conditions described in step (2) of Reaction Scheme II. The reaction may also be carried out under Swern conditions by adding a compound of Formula XXXV followed by triethylamine to a mixture of oxalyl chloride and dimethylsulfoxide in a suitable solvent such as dichloromethane. The reaction can be carried out at a sub-ambient temperature, and the product can be isolated by conventional methods.

In step (3) of Reaction Scheme III, a ketone-substituted thiazole of Formula XXXVI is converted to an oxime of Formula XXXVII. The reaction is conveniently carried out as described in step (3) of Reaction Scheme II, and the product can be isolated by conventional methods.

In step (4) of Reaction Scheme III, an oxime-substituted thiazole of Formula XXXVII is treated with a Grignard reagent to form a hydroxylamine-substituted thiazole of Formula XXXVIII. The reaction can be carried out under the conditions described in step (1) of Reaction Scheme III, and the product can be isolated by conventional methods.

In step (5) of Reaction Scheme III, a hydroxylamine of Formula XXXVIII is converted to a compound of Formula XXXIX using one of the methods described in step (9a) of Reaction Scheme I. The product can be isolated by conventional methods.

In steps (6) and (7) of Reaction Scheme III, a substituted thiazole of Formula XXXIX is first oxidized to an N-oxide of Formula XL, which is then aminated to provide a compound of Formula XLI, which is a subgenus of Formula I. Steps (6) and (7) of Reaction Scheme II can be carried out according to the methods described in steps (3) and (4) of Reaction Scheme I, and the product or a pharmaceutically acceptable salt thereof can be isolated by conventional methods.

Reaction Scheme III

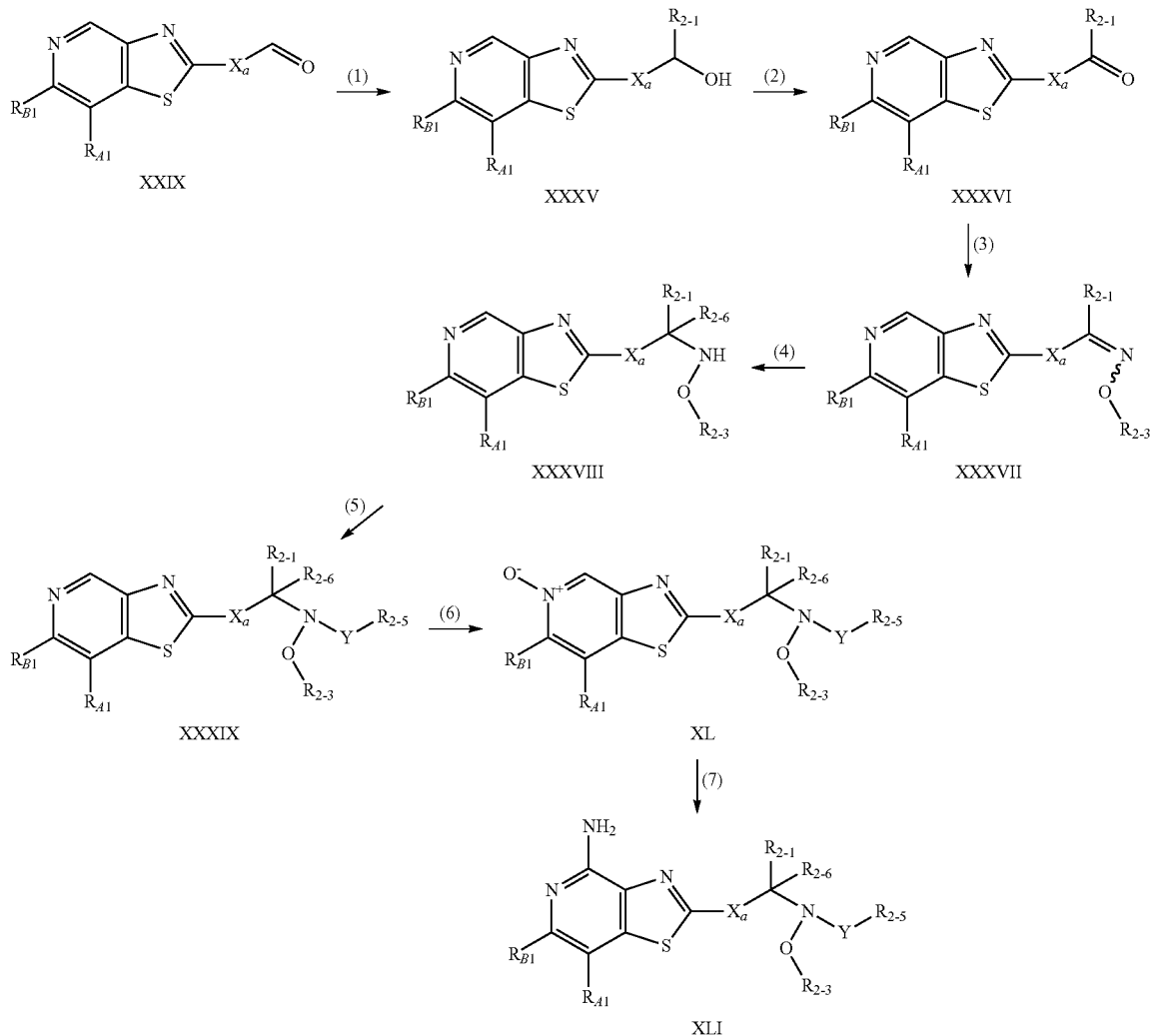

Compounds of the invention can be prepared according to Reaction Scheme IV, wherein R, $R_{2-1}$, and Z are as defined above; n is 0 or 1; Hal is —Cl, —Br, or —I; X is selected from the group consisting of $C_{1-4}$ alkylene and $C_{3-4}$ alkenylene, with the proviso that X can also be a bond when Z is —C(=N—O—$R_{2-3}$)— or —C($R_{2-6}$)(—N(—O$R_{2-3}$)—Y—$R_{2-5}$)—; and $R_{3a}$ and $R_{3b}$ are as defined below. Compounds of Formula XLII, a subgenus of Formulas I and II, can be prepared according to the methods described in Reaction Schemes I, II, and/or III beginning with a compound of Formula XV in which $R_{A1}$ and $R_{B1}$ join to form a fused benzene ring that is substituted by one, two, three, or four R groups, wherein one of the R groups is —Cl, —Br, or —I. These halogen-substituted quinolines are known or can be prepared by known methods; see, for example, U.S. Pat. No. 6,110,929 (Gerster et al).

In step (1) of Reaction Scheme IV, a halogen-substituted thiazole of Formula XLII can undergo known palladium-catalyzed coupling reactions such as the Suzuki coupling and the Heck reaction. For example, a halogen-substituted compound of Formula XLII undergoes Suzuki coupling with a boronic acid of Formula $R_{3b}$—$B(OH)_2$, an anhydride thereof, or a boronic acid ester of Formula $R_{3a}$—$B(O\text{-alkyl})_2$, wherein $R_{3a}$ is —$R_{4b}$, —$X'_a$—$R_4$, —$X'_b$—$Y'$—$R_4$, or —$X'_b$—$R_5$; where $X'_a$ is alkenylene; $X'_b$ is arylene, heteroarylene, or alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y' are as defined above. The Suzuki coupling is conveniently carried out by combining a compound of Formula XLII with a boronic acid or an ester or anhydride thereof in the presence of palladium (II) acetate, triphenylphosphine, and a base such as sodium carbonate in a suitable solvent such as n-propanol or solvent mixture such as n-propanol/water. The reaction can be carried out at an elevated temperature (e.g., 80-100° C.). Many boronic acids of Formula $R_{3a}$—$B(OH)_2$, anhydrides thereof, and boronic acid esters of Formula $R_{3a}$—$B(O\text{-alkyl})_2$ are commercially available; others can be readily prepared using known synthetic methods. See, for example, Li, W. et al, *J. Org. Chem.*, 67, 5394-5397 (2002). The product of Formula IIa, a subgenus of Formulas I and II, or a pharmaceutically acceptable salt thereof can be isolated by conventional methods.

The Heck reaction can also be used in step (1) of Reaction Scheme IV to provide compounds of Formula IIa, wherein $R_{3a}$ is —$X'_a$—$R_{4b}$ or —$X'_a$—$Y'$—$R_4$, wherein $X'_a$, Y', $R_{4b}$, and R₄ are as defined above. The Heck reaction is carried out by coupling a compound of Formula XLII with a compound of the Formula H₂C=C(H)—R₄ᵦ or H₂C=C(H)—Y'—R₄. Several of these vinyl-substituted compounds are commercially available; others can be prepared by known methods. The reaction is conveniently carried out by combining the compound of Formula XLII and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100° C.-120° C. under an inert atmosphere. The product of Formula IIa or a pharmaceutically acceptable salt thereof can be isolated using conventional methods.

Compounds of Formula IIa, wherein $R_{3a}$ is —X'_c—R₄, X'_c is alkynylene, and R₄ is as defined above, can also be prepared by palladium catalyzed coupling reactions such as the Stille coupling or Sonogashira coupling. These reactions are carried out by coupling a compound of Formula XLII with a compound of the Formula (alkyl)₃Sn—C≡C—R₄, (alkyl)₃Si—C≡C—R₄, or H—C≡C—R₄.

Some compounds of Formula IIa prepared as described above by palladium-mediated coupling reactions, wherein $R_{3a}$ is —X'_a—R₄, —X'_a—Y'—R₄, —X'_{b2}—Y'—R₄, —X'_{b2}—R₅, or —X'_c—R), where X'_{b2} is alkenylene interrupted or terminated by arylene or heteroarylene, and X'_a, X'_c, Y', R₄, and R₅ are as defined above, can undergo reduction of the alkenylene or alkynylene group present to provide compounds of Formula IIb wherein $R_{3b}$ is —X'_d—R₄, —X'_d—Y'—R₄, —X'_e—Y'—R₄, or —X'_e—R₅, where X'_d is alkylene; X'_e is alkylene interrupted or terminated by arylene or heteroarylene; and R₄, R₅, and Y' are as defined above. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product of Formula IIb, a subgenus of Formulas I and II, or a pharmaceutically acceptable salt thereof can be isolated using conventional methods.

Reaction Scheme IV

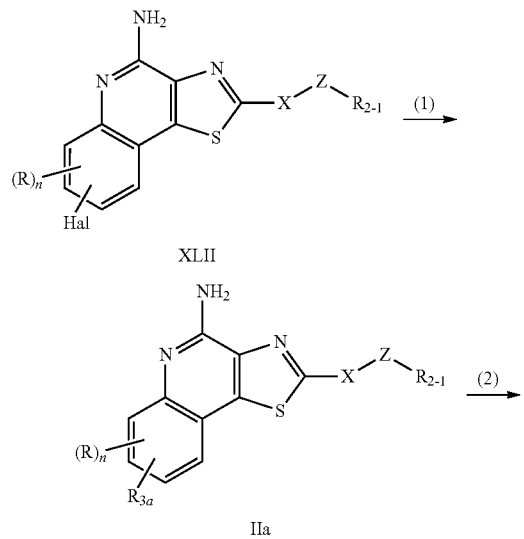

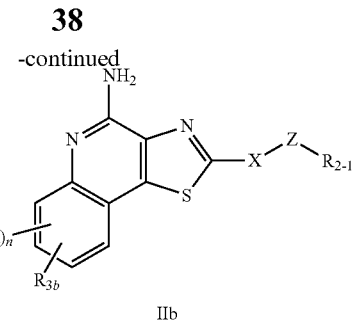

Compounds of the invention can be prepared according to Reaction Scheme V where R, $R_{2-1}$, $R_{2-2}$, X, Y, and P are as defined above; E is carbon (imidazoquinoline ring) or nitrogen (imidazonaphthyridine ring); n is 0 or 1; Bn is benzyl; $R_{3c}$ is —O—R₄, —O—X'—R₄, —O—X'—Y'—R₄, —O—X'—Y'—X'—Y'—R₄, or —O—X'—R₅, where R₄, X', Y', and R₅ are as defined above. In step (1) of Reaction Scheme V, a benzyloxyaniline or benzyloxyaminopyridine of Formula XLIII is treated with diethyl ethoxymethylenemalonate to provide an imine of Formula XLIV. The reaction is conveniently carried out by adding diethyl ethoxymethylenemalonate to a compound of Formula XLIII and heating the reaction at an elevated temperature such as 115-140° C. The reaction can be run in the absence of solvent, and the product can be isolated using conventional methods or used in the next step without isolation. Many anilines and amine-pyridines of Formula XLIII are commercially available; others can be prepared by known synthetic methods. For example, benzyloxypyridines of Formula XLIII can be prepared using the method of Holladay et al., Biorg. Med. Chem. Lett., 8, pp. 2797-2802, (1998).

In step (2) of Reaction Scheme V, an inline of Formula XLIV undergoes thermolysis and cyclization to provide a compound of Formula XLV. The reaction is conveniently carried out in a medium such as DOWTHERM A heat transfer fluid at a temperature in the range of 200 to 250° C. The product can be isolated using conventional methods.

In step (3) of Reaction Scheme V, a compound of Formula XLV is nitrated under conventional nitration conditions to provide a benzyloxy-3-nitroquinolin-4-ol or benzyloxy-3-nitro[1,5]naphthyridin-4-ol of Formula XLVI. The reaction is conveniently carried out by adding nitric acid to the compound of Formula XLV in a suitable solvent such as propionic acid and heating the mixture at an elevated temperature such as 125° C. The product can be isolated using conventional methods.

In step (4) of Reaction Scheme V, a benzyloxy-3-nitroquinolin-4-ol or benzyloxy-3-nitro[1,5]naphthyridin-4-ol of Formula XLVI is reduced to provide a 3-amino-benzyloxyquinolin-4-ol or 3-aminobenzyloxy[1,5]naphthyridin-4-ol of Formula XLVII. The reaction can be carried out by hydrogenation using a heterogeneous hydrogenation catalyst such as platinum on carbon. The hydrogenation is conveniently carried out in a Parr apparatus in a suitable solvent such as dimethylformamide (DMF). The reaction can be carried out at ambient temperature, and the product or the hydrochloride salt thereof can be isolated using conventional methods.

Steps (5) through (11) of Reaction Scheme V may be carried out according to the methods described in steps (1) through (8) of Reaction Scheme I. Step (10) of Reaction Scheme V may be carried out according to the methods of steps (6) and (7) of Reaction Scheme I or in one step as described in step (6a) of Reaction Scheme I.

In step (12) of Reaction Scheme V, the benzyl group in a hydroxylamine-substituted thiazole of Formula LIV is cleaved to provide a hydroxy group. The cleavage is conveniently carried out on a Parr apparatus under hydrogenolysis conditions using a suitable heterogeneous catalyst such as palladium or platinum on carbon in a solvent such as ethanol. Alternatively, the reaction can be carried out by transfer hydrogenation in the presence of a suitable hydrogenation catalyst The transfer hydrogenation is conveniently carried out by adding ammonium formate to a solution of a compound of Formula LIV in a suitable solvent such as ethanol in the presence of a catalyst such as palladium on carbon. The reaction is carried out at an elevated temperature, for example, the reflux temperature of the solvent. Alternatively, the cleavage can be carried out with an acid such as hydrogen bromide in a suitable solvent such as acetic acid at an elevated temperature, such as 65° C. The product of Formula LV, prepared by any of these methods, or a pharmaceutically acceptable salt thereof can be isolated using conventional methods.

In step (13) of Reaction Scheme V, a hydroxylamine-substituted thiazole of Formula LV is converted to an oxime-substituted thiazole of Formula LVI, a subgenus of Formula I, according to the method of step (9) of Reaction Scheme I.

In step (14) of Reaction Scheme V, a hydroxy-substituted oxime of Formula LVI is converted to a compound of Formula LVII, a subgenus of Formula I, using a Williamson-type ether synthesis. The reaction is effected by treating a hydroxy-substituted compound of Formula LVI with an aryl, alkyl, or arylalkylenyl halide of Formula Halide-$R_{4b}$, Halide-alkylene-$R_4$, Halide-alkylene-Y'—$R_4$, or Halide-alkylene-$R_5$ in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, and substituted fluorobenzenes. Other halides of these formulas can be prepared using conventional synthetic methods. The reaction is conveniently carried out by combining an alkyl, arylalkylenyl, or aryl halide with the hydroxy-substituted compound of Formula LVI in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the halide reagent. Alternatively, step (14) may be carried out using the Ullmann ether synthesis, in which an alkali metal aryloxide prepared from the hydroxy-substituted compound of Formula LVI reacts with an aryl halide in the presence of copper salts, to provide a compound of Formula LVII, where $R_{3c}$ is —O—$R_{4b}$, —O—$X'_f$—$R_4$, or —O—$X'_f$—Y'—$R_4$, wherein $X'_f$ is an arylene or heteroarylene, and $R_{4b}$ is as defined above. Numerous substituted and unsubstituted aryl halides are commercially available; others can be prepared using conventional methods. The product of Formula LVII, prepared by either of these methods, or a pharmaceutically acceptable salt thereof can be isolated using conventional methods.

Step (12a) of Reaction Scheme V is used to convert a hydroxylamine-substituted thiazole of Formula LIV to a compound of Formula LVIII using one of the methods described in step (9a) of Reaction Scheme I. The product of Formula LVIII, a subgenus of Formula I, or a pharmaceutically acceptable salt thereof can be isolated by conventional methods.

In step (13a) of Reaction Scheme V, the benzyl group of a compound of Formula LVIII is cleaved to provide a hydroxy-substituted compound of Formula LIX, a subgenus of Formula I, which is then converted to an ether-substituted compound of Formula LX, a subgenus of Formula I. Steps (13a) and (14a) are carried out as described above in steps (12) and (14) of Reaction Scheme V. The product or a pharmaceutically acceptable salt thereof can be isolated by conventional methods.

Isomers of the compounds of Formula XLIII and Formula XLV, wherein E is nitrogen and at a different position in the pyridine ring, can also be synthesized and can be used in Reaction Scheme V to prepare compounds of the invention.

Reaction Scheme V

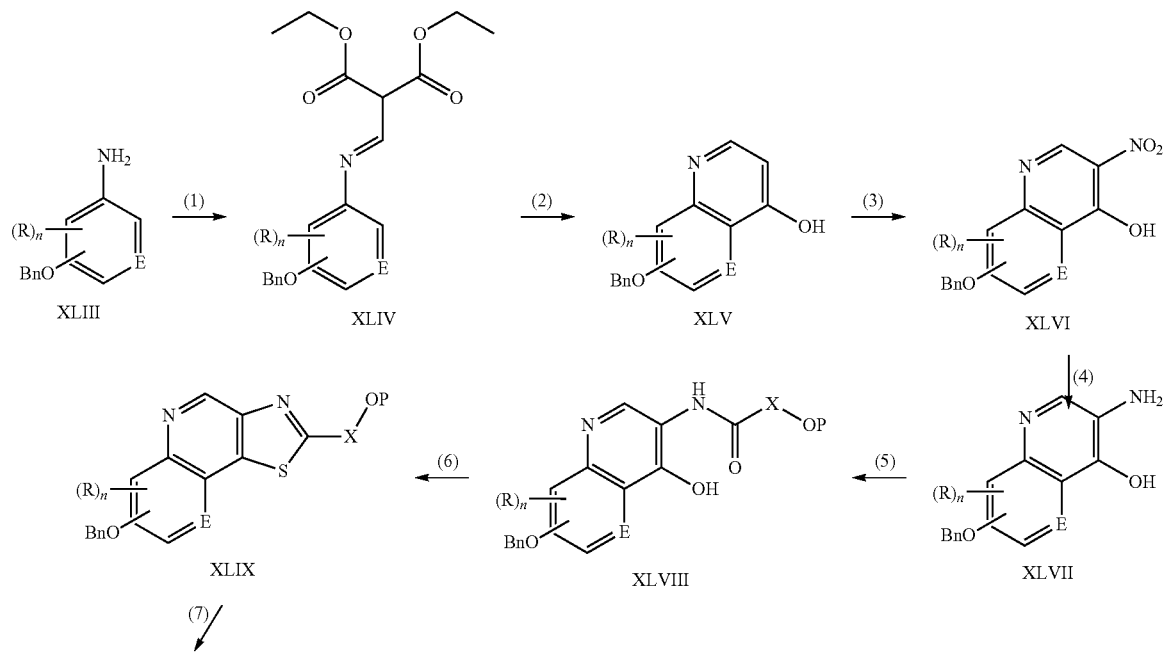

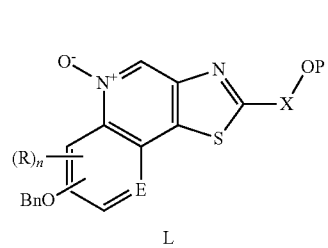
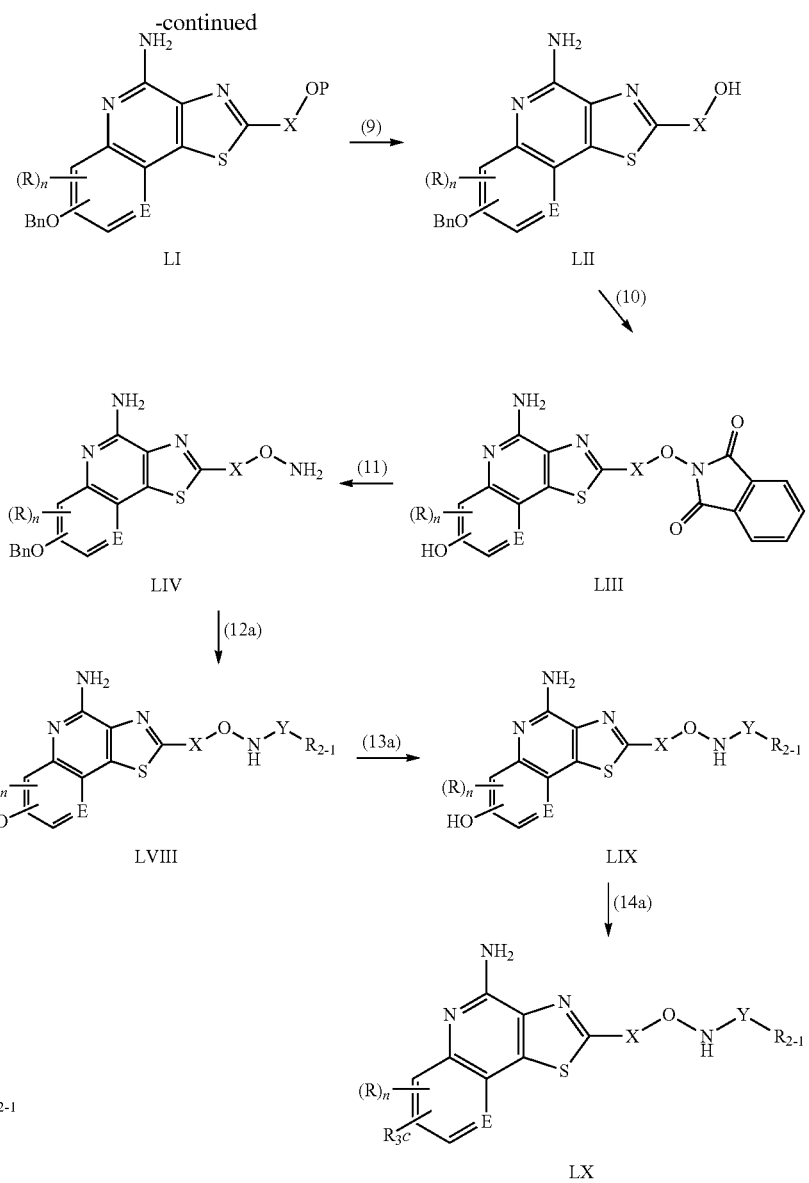

Compounds of the invention can also be prepared according to Reaction Scheme VI, wherein R, $R_{2-1}$, $R_{2-3}$, $R_{2-5}$, Bn, $R_{3c}$, P, n, and $X_a$ are as defined above. In step (1) of Reaction Scheme VI, the protecting group of a thiazole of Formula XLIXa is removed to provide a hydroxyalkyl-substituted thiazole of Formula LXI, which is oxidized in step (2) to a aldehyde-substituted thiazole of Formula LXII. In step (3) of Reaction Scheme VI, an aldehyde-substituted thiazole of Formula LXII is converted to an oxime of Formula LXIII. Steps (1), (2), and (3) of Reaction Scheme VI can be carried out according to the methods described in steps (1), (2), and (3) of Reaction Scheme II, and the product can be isolated by conventional methods.

In step (4) of Reaction Scheme VI, an oxime-substituted thiazole of Formula LXIII is oxidized and aminated to provide a compound of Formula LXIV using any of the methods described in steps (3) and (4) of Reaction Scheme I. The product, a subgenus of Formula I, can be isolated by conventional methods.

In steps (5) and (6) of Reaction Scheme I, the benzyl group of a compound of Formula LXIV is cleaved to provide a hydroxy-substituted compound of Formula LXV, which is then converted to an ether-substituted compound of Formula LXVI. Steps (5) and (6) of Reaction Scheme VI can be carried out according to the methods described in steps (12) and (14) of Reaction Scheme V. The products of Formulas LXV and LXVI, subgenera of Formula I, or pharmaceutically acceptable salts thereof, can be isolated by conventional methods.

The methods described in steps (6) and (7) of Reaction Scheme II may be applied to some compounds of Formula LXVI in steps (7) and (8) of Reaction Scheme VI to provide LXVII and LXVIII, which are subgenera of Formula I. The products or pharmaceutically acceptable salts thereof can be isolated by conventional methods.

Reaction Scheme VI

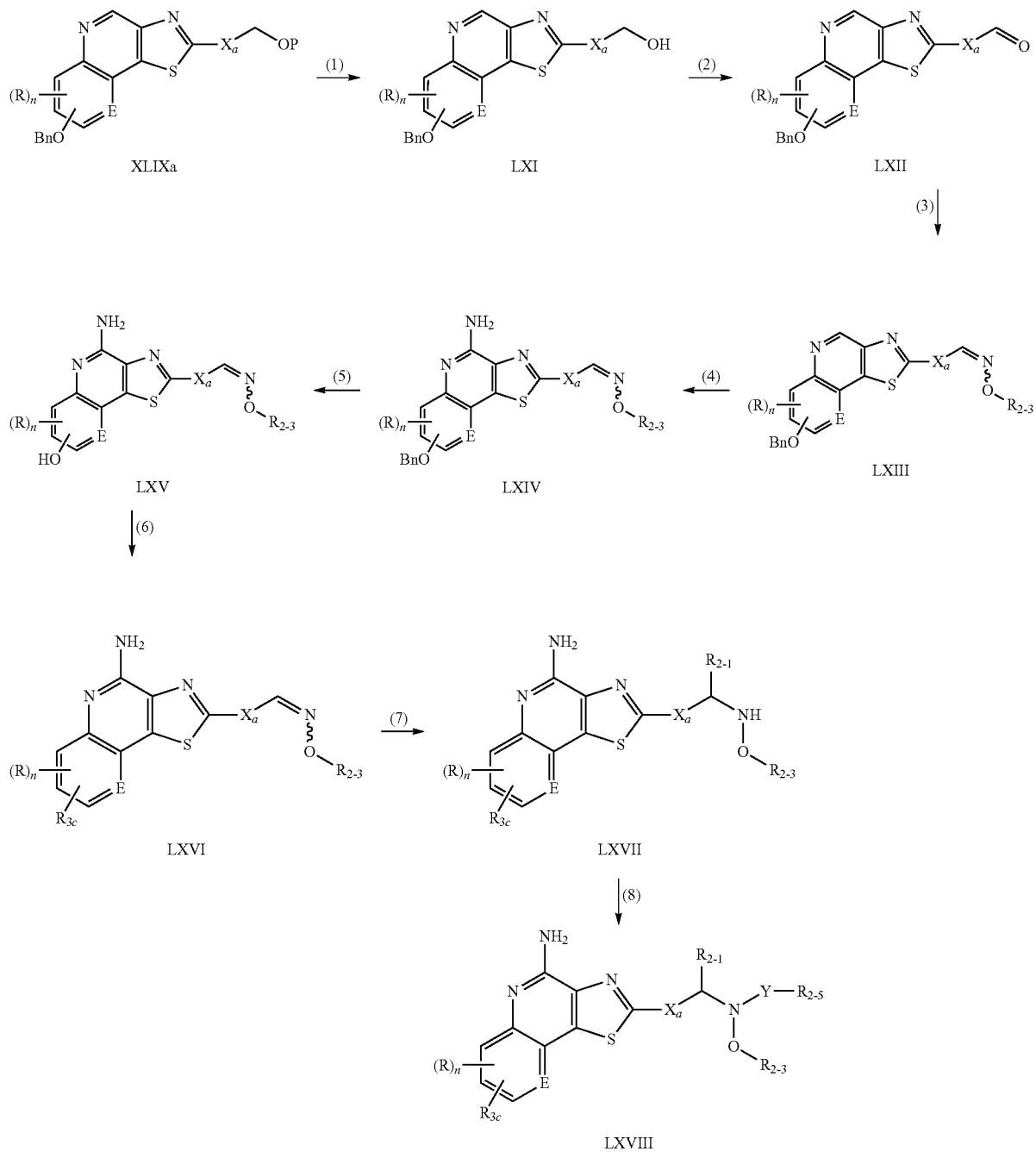

Compounds of the invention can be prepared according to Reaction Scheme VII, wherein $R_{A1}$, $R_{B1}$, $R_{2-3}$, $R_{2-5}$, $X_a$, and Y are as defined above. Compounds of Formula XXIa are prepared according to Reaction Scheme I. In Reaction Scheme VII, the chloro group of a thiazole of Formula XXIa is displaced with a hydroxylamine of formula $HN(Y—R_{2-5})OR_{2-3}$ or a salt thereof. The reaction is conveniently carried out by combining a hydroxylamine salt of the formula $HN(Y—R_{2-5})OR_{2-3}$·HCl with a compound of Formula XXIa in a suitable solvent, such as DMF, in the presence of a base such as triethylamine. The reaction can be carried out at room temperature or at an elevated temperature such as 50° C.

Some hydroxylamine salts of the formula $HN(Y—R_{2-5})OR_{2-3}$·HCl can be obtained commercially. For example N,O-dimethylhydroxylamine hydrochloride, methoxyamine hydrochloride, and N-methylhydroxylamine hydrochloride are commercially available compounds that can be used to make preferred compounds of Formula XXXIVa, wherein Y is a bond. Other hydroxylamine salts of the formula $HN(Y—R_{2-5})OR_{2-3}$·HCl can be prepared using conventional synthetic methods. The product of Formula XXXIVa, a subgenus of Formula I, or a pharmaceutically acceptable salt thereof can be isolated using conventional methods.

Reaction Scheme VII

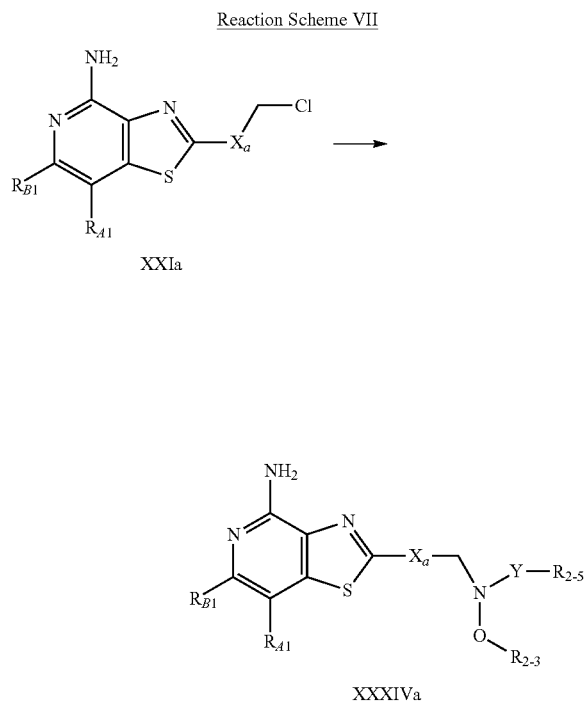

XXIa

XXXIVa

Reaction Scheme VIII

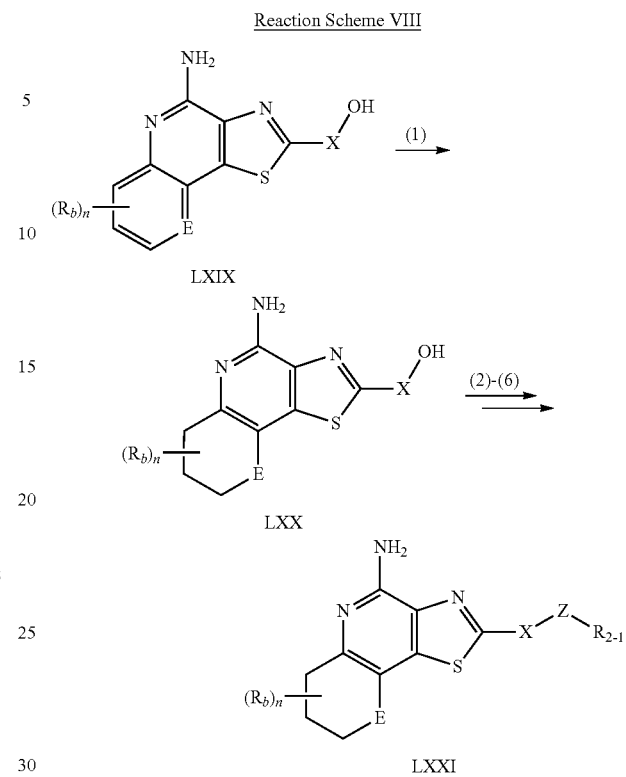

LXIX

LXX

LXXI

Compounds of the invention can be prepared according to Reaction Scheme VIII, wherein $R_{2-1}$, E, and Z are as defined above; X is selected from the group consisting of $C_{1-4}$ alkylene and $C_{3-4}$ alkenylene, with the proviso that X can also be a bond when Z is —C(=N—O—$R_{2-3}$)— or —C($R_{2-6}$)(—N(—O$R_{2-3}$)—Y—$R_{2-5}$)—; $R_b$ is selected from the group consisting of hydroxy, alkyl, alkoxy, —N($R_9$)$_2$; and n is 0 to 4. Compounds of Formula LXIX can be prepared according to Reaction Scheme I. In step (1) of Reaction Scheme VIII, a compound of Formula LXIX is reduced to a 6,7,8,9-tetrahydro compound of Formula LXX. The reaction is conveniently carried out under hetereogeneous hydrogenation conditions by adding platinum (IV) oxide to a solution of the compound of Formula LXIX in trifluoroacetic acid and placing the reaction under hydrogen pressure. The reaction can be carried out on a Parr apparatus at room temperature. The product or a pharmaceutically acceptable salt thereof can be isolated by conventional methods. Steps (2) through (6) of Reaction Scheme VIII can then be used to convert a compound of Formula LXX to a compound of Formula LXXI, a subgenus of Formula I. Steps (2) through (6) can be carried out, for example, according to steps (6), (7), (8), and (9) of Reaction Scheme I, steps (6), (7), (8), and (9a) of Reaction Scheme I, or steps (2), (3), (6), and (7) of Reaction Scheme II. The further elaboration illustrated in steps (10), (11), and (10a) of Reaction Scheme I may also be used. Compounds of Formula LXXI can also be made by treating a compound of Formula LXX according to step (6) of Reaction Scheme I and then treating the resulting chloroalkyl-substituted thiazole according to Reaction Scheme VII. The product of Formula LXXI or a pharmaceutically acceptable salt thereof can be isolated by conventional methods.

For certain embodiments, compounds of the invention can be prepared according to Reaction Scheme IX, wherein $R_{A1}$, $R_{B1}$, $R_{2-1}$, X, Z, and G are as defined above. Compounds of Formula Ia can be prepared according to the methods described above. The amino group of a compound of Formula Ia can be converted by conventional methods to a functional group such as an amide, carbamate, urea, amidine, or another hydrolyzable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")—R', —C(=N$Y_1$)—R', —CH(OH)—C(O)—O$Y_1$, —CH(O$C_{1-4}$ alkyl)$Y_0$, —CH$_2Y_2$, or —CH(CH$_3$)$Y_2$; wherein R' and R" are each independently $C_{1-10}$ alkyl, $C_{3-7}$ cycloalkyl, phenyl, or benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$; with the proviso that R" may also be hydrogen; each α-aminoacyl group is independently selected from racemic, D, or L-amino acids; $Y_1$ is hydrogen, $C_{1-6}$ alkyl, or benzyl; $Y_0$ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and $Y_2$ is mono-N—$C_{1-6}$ alkylamino, di-N,N—$C_{1-6}$alkylamino, morpholin-4-yl, piperidin-1-yl, pyrrolidin-1-yl, or 4-$C_{1-4}$ alkylpiperazin-1-yl. Particularly useful compounds of Formula III are amides derived from carboxylic acids containing one to ten carbon atoms, amides derived from amino acids, and carbamates containing one to ten carbon atoms. The reaction can be carried out, for example, by combining a compound of Formula Ia with a chloroformate or acid chloride, such as ethyl chloroformate or acetyl chloride, in the presence of a base such as triethylamine in a suitable solvent such as dichloromethane at room temperature.

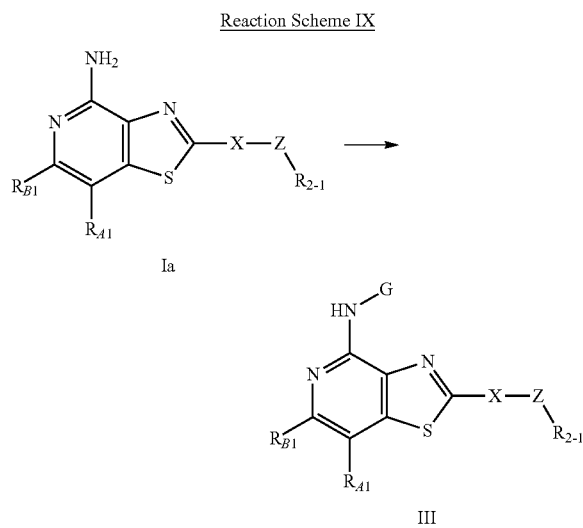

Reaction Scheme IX

Compounds of the invention can also be prepared using variations of the synthetic routes shown in Reaction Schemes I through VIII that would be apparent to one of skill in the art. For example, the synthetic route shown in Reaction Scheme IV for the preparation of quinolines having a $R_{3a}$ substituent can be used to prepare [1,5]naphthyridines having a $R_{3a}$ substituent. A halogen-substituted aminopyridine in various isomeric forms could be used as a starting material in Reaction Scheme V and be treated according to the methods of Reaction Scheme V or VI to provide a halogen-substituted thiazolo [4,5-c]naphthyridine of the invention that could be used as the starting material in Reaction Scheme IV. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m² to about 5.0 mg/m², computed according to the Dubois method, in which the body surface area of a subject (m²) is computed using the subject's body weight: $m^2 = (wt\ kg^{0.425} \times height\ cm^{0.725}) \times$ 0.007184, although in some embodiments the methods may be performed by administering a compound or salt or composition in a dose outside this range. In some of these embodiments, the method includes administering sufficient compound to provide a dose of from about 0.1 mg/m² to about 2.0 mg/m² to the subject, for example, a dose of from about 0.4 mg/m² to about 1.2 mg/m².

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *Pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m² to about 5.0 mg/m², (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m² to about 2.0 mg/m² to the subject, for example, a dose of from about 0.4 mg/m² to about 1.2 mg/m².

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m² to about 5.0 mg/m², (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Example 1

Acetone O-[(4-amino[1,3]thiazolo[4,5-c]quinolin-2-yl)methyl]oxime

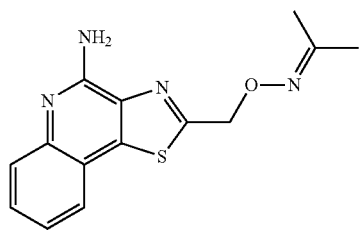 [SMILES: CC(C)=NOCc1nc2c(N)nc3ccccc3c2s1]

Part A

3-Chloroperoxybenzoic acid (mCPBA) (34.7 grams (g) of 77% purity, 155 millimoles (mmol)) was added over a period of 15 minutes to a solution of [1,3]thiazolo[4,5-c]quinolin-2-ylmethyl acetate (U.S. Pat. No. 6,110,929, Example 37 Parts A and B, 20.0 g, 77.4 mmol) in chloroform (500 milliliters (mL)), and the reaction was stirred for two hours at room temperature and subsequently washed with aqueous sodium carbonate (500 mL of 10% weight/weight (w/w)). The organic layer was dried over magnesium sulfate and filtered to provide a solution of (5-oxido[1,3]thiazolo[4,5-c]quinolin-2-yl)methyl acetate in chloroform.

Part B

Trichloroacetyl isocyanate (21.9 g, 13.8 mL, 116 mmol) was added to the solution from Part A, and the reaction was stirred at room temperature for two hours. An analysis by liquid chromatography/mass spectrometry (LC/MS) indicated the presence of starting material, and additional trichloroacetyl isocyanate (7 mL) was added. The reaction was stirred for 30 minutes at room temperature, and the solvent was removed under reduced pressure. The residue was dissolved in ethanol (500 mL), and potassium ethoxide (6.52 g, 77.4 mmol) was added. The resulting mixture was stirred at room temperature overnight, and a precipitate formed. The precipitate was isolated by filtration, washed with ethanol, and dried in a vacuum oven for three days to provide 8.16 g of a 50:50 mixture of (4-amino[1,3]thiazolo[4,5-c]quinolin-2-yl)methanol and (4-amino[1,3]thiazolo[4,5-c]quinolin-2-yl) methyl acetate as a tan solid. The filtrate was concentrated under reduced pressure, and the residue was mixed with ethanol (100 mL), filtered, washed with ethanol, and dried in a vacuum oven for three days to provide an additional 7.42 g of product.

Part C

Lithium hydroxide monohydrate (2.50 g, 59.7 mmol) was added to a solution of the mixture from Part B (8.16 g) in tetrahydrofuran (THF) (75 mL), methanol (150 mL), and water (75 mL), and the reaction mixture was stirred for three hours at room temperature. A solid formed, which was isolated by filtration, washed with water, and dried in a vacuum oven overnight to provide 3.5 g of (4-amino[1,3]thiazolo[4,5-c]quinolin-2-yl)methanol as a tan solid. The THF and methanol were removed from the filtrate under reduced pressure, and the resulting mixture was filtered to isolate the solid, which was washed with water and dried in a vacuum oven overnight to provide an additional 2.15 g of product The two batches of solid were mixed with material from another run.

Part D

Thionyl chloride (4.92 mL, 67.6 mmol) was added to a suspension of (4-amino[1,3]thiazolo[4,5-c]quinolin-2-yl)methanol (13 g, 56 mmol) in 1,2-dichloroethane (300 mL), and the reaction was heated at reflux for two hours and then concentrated under reduced pressure to provide 16 g of 2-(chloromethyl)[1,3]thiazolo[4,5-c]quinolin-4-amine hydrochloride as a yellow solid.

Part E

Triethylamine (7.3 mL, 52 mmol) was added to a solution of N-hydroxyphthalimide (3.42 g, 21.0 mmol) in N,N-dimethylformamide (DMF) (50 mL). 2-(Chloromethyl)[1,3]thiazolo[4,5-c]quinolin-4-amine hydrochloride (5.0 g, 18 mmol) was added to the resulting deep red solution, and the reaction was stirred overnight at ambient temperature. A precipitate formed and was isolated by filtration, washed with dichloromethane, and dried in a vacuum oven to provide 3.34 g of 2-[(4-amino[1,3]thiazolo[4,5-c]quinolin-2-yl)methoxy]-1H-isoindole-1,3(2H)-dione as a tan solid. The filtrate was concentrated under reduced pressure, and the residue was mixed with dichloromethane, filtered, washed with dichloromethane, and dried in a vacuum oven overnight to provide an additional 2.06 g of product.

Part F

Hydrazine (2.25 mL, 71.7 mmol) was added to a suspension of 2-[(4-amino[1,3]thiazolo[4,5-c]quinolin-2-yl)methoxy]-1H-isoindole-1,3(2H)-dione (5.4 g, 14 mmol) in ethanol (200 mL), and the reaction was heated at reflux for one hour and filtered hot to remove a solid. The filtrate was concentrated under reduced pressure and further dried in a vacuum oven overnight The resulting solid (4.89 g) was triturated with ethanol (200 mL) for two hours, filtered, washed with ethanol, and dried in a vacuum oven to provide 3.05 g of 2-(aminooxy)methyl[1,3]thiazolo[4,5-c]quinolin-4-amine as an orange solid containing some phthalhydrazide. The filtrate was concentrated under reduced pressure to provide an additional 1.91 g of the product mixture.

Part G

Methanol (50 mL) and acetone (50 mL) were added to the material from Part F (1 g), and the reaction mixture was stirred at room temperature for 1.5 hours. Silica gel was added, and the mixture was concentrated under reduced pressure. The residue was purified by column chromatography using a HORIZON HPFC system (an automated, modular high-performance flash purification product available from Biotage, Inc, Charlottesville, Va., USA) (silica cartridge, eluting with 2% methanol in chloroform). The resulting yellow solid (730 mg) was recrystallized from acetonitrile (30 mL).

The crystals were isolated by filtration, washed with acetonitrile, and dried in a vacuum oven to provide 267 mg of acetone O-(4-amino[1,3]thiazolo[4,5-c]quinolin-2-ylmethyl)oxime as yellow crystals, mp 152-153° C.

Anal. calcd for $C_{14}H_{14}N_4OS$: C, 58,72; H, 4.93; N, 19.57. Found: C, 58.65; H, 4.79; N, 19.81.

Example 2

Acetone O-(4-amino-7-bromo[1,3]thiazolo[4,5-c]quinolin-2-ylmethyl)oxime

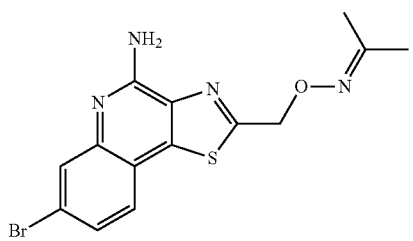 [SMILES: CC(C)=NOCc1nc2c(N)nc3cc(Br)ccc3c2s1]

Part A

Diethyl ethoxymethylenemalonate (677 g, 3.13 moles (mol)) was added to 3-bromoaniline (491 g, 2.85 mol) over a period of one hour, the temperature rose to 60° C. during the addition. The reaction was then heated at 115° C. for 30 minutes, 125° C. for 30 minutes, and 140° C. for 15 minutes while ethanol was distilled from the reaction. The reaction temperature was adjusted to 130° C., and the reaction mixture was added over a period of 45 minutes to heated DOWTHERM A heat transfer fluid (5 liters (L), 250° C.) while maintaining the temperature of the heat transfer fluid between 242° C. and 250° C. A precipitate formed at the end of the addition. The reaction mixture was heated at about 250° C. for one hour and then cooled to 80° C. Concentrated hydrochloric acid (500 mL) was added, and the reaction mixture was heated at 110° C. for five hours, 125° C. for two hours, and 150° C. for an addition two hours, and then allowed to cool to room temperature overnight. The mixture was then heated to 200° C. over a period of two hours, further heated to 250° C., maintained at 250° C. for one hour, and allowed to cool to room temperature. A precipitate was present and was isolated by filtration, washed sequentially with heptane (2 L), ethanol (1 L), and diethyl ether (1 L) to provide 604 g of 7-bromo quinolin-4-ol as a dark red solid.

Part B

A solution of 7-bromoquinolin-4-ol (594 g, 2.65 mol) in propionic acid (5 L) was heated to 120° C., and nitric acid (215 mL of 16 molar (M)) was added dropwise over a period of 2.5 hours while maintaining the temperature in the range of 119° C. to 130° C. The reaction was then cooled to 60° C. and filtered to collect a solid, which was washed sequentially with water (3×500 mL), 2-propanol (500 mL), and diethyl ether (300 mL), and pulled dry with vacuum filtration to provide 447 g of 7-bromo-3-nitroquinolin-4-ol as a tan powder.

Part C

A Parr vessel was charged with 7-bromo-3-nitroquinolin-4-ol (272 g, 1.01 mol), DMF (2.7 L), and 5% platinum on carbon (21 g), and the mixture was placed under hydrogen pressure (50 psi, $3.4 \times 10^5$ Pa) for three hours. The mixture was filtered through a layer of CELITE filter agent, and the filter cake was washed with DMF (500 mL). The filtrate was cooled to approximately 0° C., and anhydrous hydrogen chloride gas (approximately 70 g) was dispersed through the solution for about five minutes. A precipitate formed and was isolated by filtration, washed with acetone (500 mL), and dried on the filter funnel to provide 224 g of 7-bromo-4-hydroxyquinolin-3-aminium chloride as a tan solid.

Part D

Triethylamine (161 g, 1.59 mol) was added to a suspension of 7-bromo-4-hydroxyquinolin-3-aminium chloride (224 g, 0.815 mol) in dichloromethane (2.25 L), and the mixture was cooled to approximately 0° C. Acetoxyacetyl chloride (112 g, 0.820 mol) was added over a period of one hour. The reaction was stirred at room temperature for one hour and then allowed to stand for three days. A solid was present and was isolated by filtration and pressed dry. The solid was stirred in deionized water (2 L) for two hours, isolated by filtration, dried overnight on the filter funnel, and further dried in a vacuum oven at 60 to 70° C. to provide 223 g of 2-[(7-bromo-4-hydroxyquinolin-3-yl)amino]-2-oxoethyl acetate as a reddish brown solid.

Part E

Phosphorous pentasulfide (146 g, 0.328 mol) was added to a suspension of 2-[(7-bromo-4-hydroxyquinolin-3-yl)amino]-2-oxoethyl acetate (222 g, 0.655 mol) in pyridine (2 L), and the reaction was heated at reflux for 1.5 hours. A portion of the pyridine (1.8 L) was removed by vacuum filtration. A mixture of saturated aqueous sodium carbonate (750 mL) and deionized water (750 mL) was slowly added, and then 750 mL of a mixture of water and pyridine was removed by vacuum filtration. The remaining mixture was stirred overnight. A solid was present and was isolated by filtration, washed with water (3×500 mL), and dried on the filter funnel to provide 220 g of (7-bromo[1,3]triazolo[4,5-c]quinolin-2-yl)methyl acetate as a brown solid, which was used in the next step without purification.

Part F

Lithium hydroxide monohydrate (12.4 g, 297 mmol) was added to a solution of (7-bromo[1,3]triazolo[4,5-c]quinolin-2-yl)methyl acetate (50.0 g, 148 mmol) in THF (250 mL), methanol (500 mL), and water (250 mL), and the reaction mixture was stirred for one hour at room temperature. The THF and methanol were removed under reduced pressure. A precipitate formed, which was isolated by filtration, washed sequentially with water and diethyl ether, and dried in a vacuum oven overnight to provide 35.5 g of (7-bromo[1,3]thiazolo[4,5-c]quinolin-2-yl)methanol as a greenish-brown solid.

Part G

N-Hydroxyphthalimide (4.15 g, 25.4 mmol) and triphenylphosphine (6.66 g, 25.4 mmol) were added to a suspension of (7-bromo[1,3]thiazolo[4,5-c]quinolin-2-yl)methanol (5.00 g, 16.9 mmol) in THF (170 mL). Diethyl azodicarboxylate (4.43 g, 25.4 mmol) was added dropwise, and the resulting solution was stirred at room temperature for 1.5 hours. A precipitate formed and was isolated by filtration, washed with THF, and dried in a vacuum oven to provide 5.59 g of 2-[(7-bromo[1,3]thiazolo[4,5-c]quinolin-2-yl)methoxy]-1H-isoindole-1,3(2H)-dione.

Part H

Hydrazine hydrate (3.17 g, 63.4 mmol) was added to a suspension of 2-[(7-bromo[1,3]thiazolo[4,5-c]quinolin-2-yl)methoxy]-1H-isoindole-1,3(2H)-dione (5.58 g, 12.7 mmol) in ethanol (50 mL), and the reaction was stirred at room temperature for three hours. The solvent was removed under reduced pressure, and the crude mixture containing 2-(aminooxy)methyl-7-bromo[1,3]triazolo[4,5-c]quinoline was used in the next step without purification.

Part I

Methanol (80 mL) and acetone (40 mL) were added to the material from Part H, and the reaction mixture was stirred at room temperature for 17 hours. Silica gel was added, and the mixture was concentrated under reduced pressure. The residue was purified by column chromatography using a HORIZON HPFC system (silica cartridge, eluting with 5% methanol in dichloromethane). The resulting yellow solid (6.06 g) was triturated with methanol (150 mL), filtered, washed with methanol, and dried in a vacuum oven to provide 1.88 g of acetone O-(7-bromo[1,3]thiazolo[4,5-c]quinolin-2-ylmethyl)oxime as a tan solid. The filtrate was concentrated under reduced pressure, and the residue was triturated with methanol (50 mL), filtered, washed with methanol, and dried in a vacuum oven to provide an additional 1.09 g of product A precipitate formed in the filtrate and was isolated by filtration, washed with methanol, and dried in a vacuum oven to provide an additional 665 mg of product.

Part J mCPBA (5.50 g of 77% purity, 24.6 mmol) was added to a solution of acetone O-(7-bromo[1,3]thiazolo[4,5-c]quinolin-2-ylmethyl)oxime (3.44 g, 9.82 mmol) in chloroform (100 mL), and the reaction was stirred for 1.5 hours at room temperature and subsequently washed with aqueous sodium carbonate (100 mL of 10% w/w). The organic layer was dried over magnesium sulfate and filtered to provide a solution of acetone O-(7-bromo-5-oxido[1,3]thiazolo[4,5-c]quinolin-2-ylmethyl)oxime in chloroform.

Part K

Trichloroacetyl isocyanate (4.63 g, 2.93 mL, 24.6 mmol) was added to the solution from Part J with stirring, and the reaction was stirred at room temperature for three hours. The solvent was removed under reduced pressure. The residue was dissolved in ethanol (100 mL), and potassium ethoxide (0.827 g, 9.82 mmol) was added. The resulting mixture was stirred at room temperature for 20 hours; a precipitate began to form after one hour of stirring. The precipitate was isolated by filtration, washed with ethanol, and dried in a vacuum oven to provide 1.86 g of acetone O-(4-amino-7-bromo[1,3]thiazolo[4,5-c]quinolin-2-ylmethyl)oxime as a brown solid. The filtrate was concentrated under reduced pressure, and the residue was purified by column chromatography using a HORIZON HPFC system (silica cartridge, eluting with 3-10% methanol in dichloromethane). The resulting solid was recrystallized from 1:1:1 acetonitrile/methanol/dichloromethane. The crystals were isolated by filtration, washed with dichloromethane, and dried in a vacuum oven to provide an additional 0.354 g of acetone O-(4-amino-7-bromo[1,3]thiazolo[4,5-c]quinolin-2-ylmethyl)oxime as light brown crystals, mp 211-213° C.

Anal. calcd for $C_{14}H_{13}BrN_4OS$: C, 46.04; H, 3.59; N, 15.34. Found: C, 45.89; H, 3.36; N, 15.38.

Example 3

4-Amino-7-bromo[1,3]thiazolo[4,5-c]quinoline-2-carbaldehyde O-methyloxime

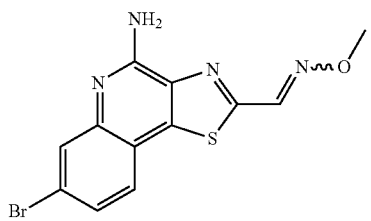 [SMILES: CON=Cc1nc2c(N)nc3cc(Br)ccc3c2s1]

Part A

Dess-Martin periodinane (2.16 g, 5.08 mol, [1,1,1-tris(acetyloxy)-1,1-dihydro-1,2-benziodoxol-3-(1H)-one]) was added to a suspension of (7-bromo[1,3]thiazolo[4,5-c]quinolin-2-yl)methanol (prepared in Part F of Example 2, 1.0 g, 3.4 mmol) in dichloromethane (30 mL), and the resulting suspension was stirred at room temperature for 1.5 hours. The reaction mixture was filtered to isolate solid, which was washed with dichloromethane and diethyl ether to provide 877 mg of 7-bromo[1,3]thiazolo[4,5-c]quinoline-2-carbaldehyde as a brown solid.

Part B

Methoxylamine hydrochloride (0.500 g, 5.98 mmol) was added to a suspension of 7-bromo[1,3]thiazolo[4,5-c]quinoline-2-carbaldehyde (877 mg, 2.99 mmol) in methanol (10 mL), and the suspension was stirred at room temperature for 17 hours. The reaction mixture was filtered to isolate solid, which was washed with methanol to provide 607 mg of tan solid. The filtrate was concentrated under reduced pressure to provide an additional 660 mg of tan solid. The two solids were combined to provide 1.2 g of 7-bromo[1,3]thiazolo[4,5-c]quinoline-2-carbaldehyde O-methyloxime as a 1:1 mixture of isomers.

Part C mCPBA (1.68 g of 77% purity, 7.48 mmol) was added to a solution of the material from Part B in chloroform (30 mL), and the reaction was stirred for 30 minutes at room temperature. An analysis by LC/MS indicated mat no reaction had taken place, and potassium hydroxide (21 mL of 0.5 N in methanol) was added. The reaction was stirred at ambient temperature for one hour. An analysis by LC/MS indicated that no reaction had taken place. The solvent was removed under reduced pressure, and the residue was diluted with dichloromethane (100 mL). The resulting solution was washed with a mixture of saturated aqueous sodium bicarbonate (50 mL) and water (50 mL), and the aqueous layer was extracted with dichloromethane (100 mL). The combined organic fractions were dried over magnesium sulfate, filtered, and concentrated under reduced pressure. The residue was dissolved in chloroform (30 mL), and mCPBA (1.68 g, 7.48 mmol) was added. The reaction was stirred for two hours and then washed with aqueous sodium carbonate (50 mL of 10% w/w). The layers were allowed to separate overnight. Some solid was present and was isolated by filtration. The organic layer was separated, dried over magnesium sulfate, filtered, and concentrated under reduced pressure. The residue was combined with the isolated solid to provide 7-bromo-5-oxido[1,3]triazolo[4,5-c]quinoline-2-carbaldehyde O-methyloxime.

Part D

Trichloroacetyl isocyanate (1.41 g, 0.891 mL, 7.48 mmol) was added to a solution of the material from Part C in chloroform (30 mL) with stirring, and the reaction was stirred at room temperature for one hour. An analysis by LC/MS indicated the presence of starting material, and additional trichloroacetyl isocyanate (0.200 mL) was added. The reaction was stirred for 1.5 hours at room temperature, and then the solvent was removed under reduced pressure. The residue was dissolved in ethanol (30 mL), and potassium ethoxide (0.252 g, 2.99 mmol) was added. The resulting mixture was stirred at room temperature for 18 hours; the solvent was removed under reduced pressure. The residue was purified by column chromatography using a HORIZON HPFC system (silica cartridge, eluting with 3 to 7% methanol in dichloromethane). The resulting solid was triturated with methanol (30 mL) and isolated by filtration to provide 60 mg of 4-amino-7-bromo[1,3]thiazolo[4,5-c]quinoline-2-carbaldehyde O-methyloxime as a yellow solid in a 4:1 mixture of isomers, mp 262-264° C.

Anal. calcd for $C_{12}H_9BrN_4OS$: C, 42.74; H, 2.69; N, 16.62. Found: C, 42.50; H, 2.62; N, 16.56.

Examples 4-72

An aldehyde or ketone from the table below (1.1 equivalents. 0.11 mmol) was added to a test tube containing a solution of 2-(aminooxy)methyl[1,3]thiazolo[4,5-c]quinolin-4-amine (prepared in Parts A through F of Example 1, 40 mg, 0.1 mmol) in methanol (1 mL). The test tube was capped and placed on a shaker at room temperature for 84 hours. The solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound Reversed phase prep HPLC was performed with non-linear gradient elution from 5-95% B where A is 0.05% trifluoroacetic acid/water and B is 0.05% trifluoroacetic acid/acetonitrile. Fractions were collected by mass-selective triggering. The table below shows the ketone or aldehyde used for each example, the structure of the resulting compound, and the observed accurate mass for the isolated trifluoroacetate salt. While the structures in the table for R are drawn as the trans isomer, each Example compound may contain cis isomer, may be completely cis isomer, or may be completely trans isomer, as the isomer(s) present was not determined.

Examples 4-72

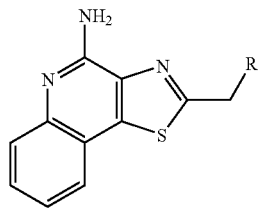

| Example | Reagent | R | Measured Mass (M + H) |
|---|---|---|---|
| 4 | 2-Hydroxyacetaldehyde | (CH=N-O-CH₂-)–CH₂OH | 289.0768 |
| 5 | Cyclopropanecarboxaldehyde | (CH=N-O-CH₂-)–cyclopropyl | 299.0966 |
| 6 | Butyraldehyde | (CH=N-O-CH₂-)–CH₂CH₂CH₃ | 301.1127 |
| 7 | Isobutyraldehyde | (CH=N-O-CH₂-)–CH(CH₃)₂ | 301.1113 |
| 8 | Trimethylacetaldehyde | (CH=N-O-CH₂-)–C(CH₃)₃ | 315.1289 |
| 9 | Isovaleraldehyde | (CH=N-O-CH₂-)–CH₂CH(CH₃)₂ | 315.1290 |

-continued

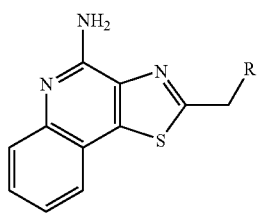

| Example | Reagent | R | Measured Mass (M + H) |
|---|---|---|---|
| 10 | 3-Hydroxybutanal | (CH(OH)CH₃ substituted methoxime) | 317.1062 |
| 11 | 3-Furaldehyde | (3-furyl methoxime) | 325.0759 |
| 12 | Furfural | (2-furyl methoxime) | 325.0761 |
| 13 | Tetrahydrofuran-3-carboxaldehyde | (tetrahydrofuran-3-yl methoxime) | 329.1083 |
| 14 | Benzaldehyde | (phenyl methoxime) | 335.0981 |
| 15 | Picolinaldehyde | (2-pyridyl methoxime) | 336.0932 |
| 16 | 1-Methylpyrrole-2-carboxaldehyde | (1-methylpyrrol-2-yl methoxime) | 338.1083 |
| 17 | 1-Methyl-2-Imidazolecarboxaldehyde | (1-methylimidazol-2-yl methoxime) | 339.1051 |
| 18 | Cyclohexanecarboxaldehyde | (cyclohexyl methoxime) | 341.1432 |

-continued
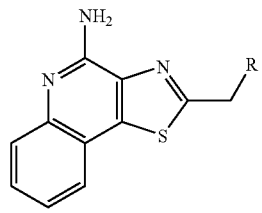
| Example | Reagent | R | Measured Mass (M + H) |
|---|---|---|---|
| 19 | 2-Thiazolecarboxyaldehyde | | 342.0491 |
| 20 | m-Tolualdehyde | | 349.1153 |
| 21 | o-Tolualdehyde | | 349.1139 |
| 22 | p-Tolualdehyde | | 349.1146 |
| 23 | Phenylacetaldehyde | | 349.1143 |
| 24 | 2-Fluorobenzaldehyde | | 353.0878 |
| 25 | 4-Fluorobenzaldehyde | | 353.0895 |

-continued
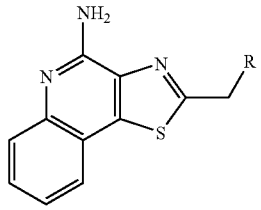
| Example | Reagent | R | Measured Mass (M + H) |
|---|---|---|---|
| 26 | 2-Cyanobenzaldehyde | 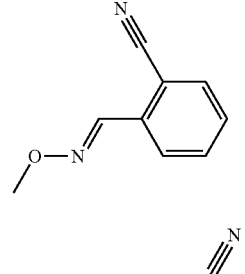 | 360.0936 |
| 27 | 3-Cyanobenzaldehyde | 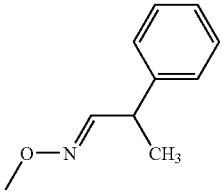 | 360.0928 |
| 28 | 2-Phenylpropionaldehyde | 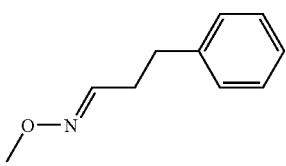 | 363.1278 |
| 29 | 3-Phenylpropionaldehyde | 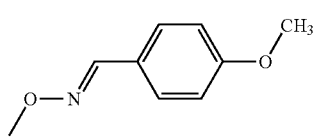 | 363.1288 |
| 30 | p-Anisaldehyde | 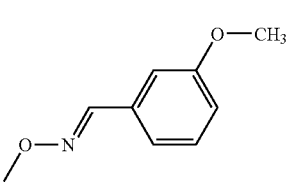 | 365.1084 |
| 31 | 3-Methoxybenzaldehyde | 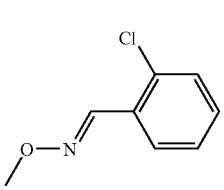 | 365.1091 |
| 32 | 2-Chlorobenzaldehyde | | 369.0594 |

-continued
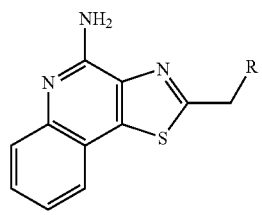
| Example | Reagent | R | Measured Mass (M + H) |
|---|---|---|---|
| 33 | 3-Chlorobenzaldehyde | 3-Cl-C6H4-CH=N-O-CH3 | 369.0584 |
| 34 | 4-Chlorobenzaldehyde | 4-Cl-C6H4-CH=N-O-CH3 | 369.0567 |
| 35 | 3,5-Difluorobenzaldehyde | 3,5-F2-C6H3-CH=N-O-CH3 | 371.0780 |
| 36 | 2,5-Difluorobenzaldehyde | 2,5-F2-C6H3-CH=N-O-CH3 | 371.0809 |
| 37 | 2,6-Difluorobenzaldehyde | 2,6-F2-C6H3-CH=N-O-CH3 | 371.0791 |
| 38 | 3,4-Difluorobenzaldehyde | 3,4-F2-C6H3-CH=N-O-CH3 | 371.0811 |
| 39 | Ethyl 2-formyl-1-cyclopropanecarboxylate | cyclopropyl(CO2CH2CH3)-CH=N-O-CH3 | 371.1154 |

-continued
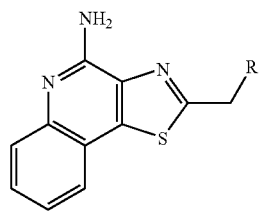
| Example | Reagent | R | Measured Mass (M + H) |
|---|---|---|---|
| 40 | 3-Phenyl butanal | | 377.1448 |
| 41 | 3-Hydroxy-4-methoxybenzaldehyde | | 381.1055 |
| 42 | 2-Naphthaldehyde | | 385.1135 |
| 43 | 2-Quinolinecarboxaldehyde | | 386.1081 |
| 44 | 3-Chloro-4-fluorobenzaldehyde | | 387.0500 |
| 45 | 2,4-Dimethoxybenzaldehyde | | 395.1193 |
| 46 | 2,5-Dimethoxybenzaldehyde | | 395.1194 |

-continued
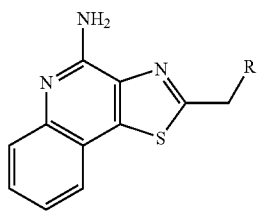
| Example | Reagent | R | Measured Mass (M + H) |
|---|---|---|---|
| 47 | 2,6-Dimethoxybenzaldehyde | | 395.1198 |
| 48 | 3,4-Dimethoxybenzaldehyde | | 395.1183 |
| 49 | 3,5-Dimethoxybenzaldehyde | | 395.1207 |
| 50 | 3,5-Dichlorobenzaldehyde | | 403.0218 |
| 51 | 2,3-Dichlorobenzaldehyde | | 403.0215 |
| 52 | 2,4-Dichlorobenzaldehyde | | 403.0224 |

-continued

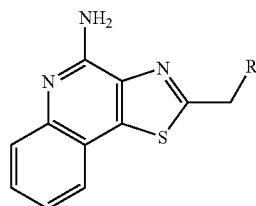

| Example | Reagent | R | Measured Mass (M + H) |
|---|---|---|---|
| 53 | 2,6-Dichlorobenzaldehyde | 2,6-dichlorophenyl-CH=N-O-CH₃ | 403.0201 |
| 54 | 3,4-Dichlorobenzaldehyde | 3,4-dichlorophenyl-CH=N-O-CH₃ | 403.0219 |
| 55 | Syringaldehyde | 3,5-dimethoxy-4-hydroxyphenyl-CH=N-O-CH₃ | 411.1093 |
| 56 | Acetone | (CH₃)₂C=N-O-CH₃ | 287.0983 |
| 57 | 2-Butanone | CH₃-C(=N-O-CH₃)-CH₂CH₃ | 301.1134 |
| 58 | Hydroxyacetone | CH₃-C(=N-O-CH₃)-CH₂OH | 303.0915 |
| 59 | Cyclopentanone | cyclopentylidene=N-O-CH₃ | 313.1120 |
| 60 | Cyclopropyl methyl ketone | CH₃-C(=N-O-CH₃)-cyclopropyl | 313.1114 |

-continued
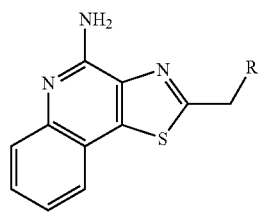
| Example | Reagent | R | Measured Mass (M + H) |
|---|---|---|---|
| 61 | 3-Pentanone | ![R]  (H3C-CH2-C(=N-O-CH3)-CH2-CH3) | 315.1301 |
| 62 | 4-Hydroxy-2-butanone | (H3C-C(=N-O-CH3)-CH2-OH) | 317.1067 |
| 63 | Acetoin | (H3C-C(=N-O-CH3)-CH(OH)-CH3) | 317.1074 |
| 64 | Acetylcyclobutane | (H3C-C(=N-O-CH3)-cyclobutyl) | 327.1295 |
| 65 | Cyclohexanone | (cyclohexylidene=N-O-CH3) | 327.1286 |
| 66 | 3-Acetylpyrrole | (H3C-C(=N-O-CH3)-pyrrol-3-yl) | 338.1092 |
| 67 | 2'-Hydroxyacetophenone | (H3C-C(=N-O-CH3)-(2-hydroxyphenyl)) | 365.1084 |
| 68 | 4'-Hydroxyacetophenone | (H3C-C(=N-O-CH3)-(4-hydroxyphenyl)) | 365.1096 |

-continued

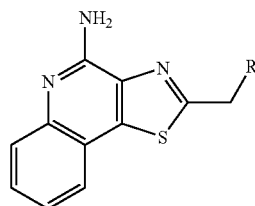

| Example | Reagent | R | Measured Mass (M + H) |
|---|---|---|---|
| 69 | m-Hydroxyacetophenone | ![structure with OH, H3C, O-N] | 365.1094 |
| 70 | 1-Acetyl-4-piperidone | ![structure with H3C, C=O, piperidine, O-N] | 370.1313 |
| 71 | 4-Phenylcyclohexanone | ![structure with phenyl, piperidine, O-N] | 403.1593 |
| 72 | 1-Benzyl-4-piperidone | ![structure with benzyl, piperidine, O-N] | 418.1700 |

Examples 73-114

Part A

A modification of the methods described in Parts F and G of Example 2 were used to convert ([1,3]thiazolo[4,5-c]quinolin-2-yl)methyl acetate to 2-[([1,3]thiazolo[4,5-c]quinolin-2-yl)methoxy]-1H-isoindole-1,3(2H)-dione. The reaction in Part F was stirred for 3.5 hours at ambient temperature, and diisopropyl azodicarboxylate was used instead of diethyl azodicarboxylate in Part G.

Part B

Hydrazine (3.4 g, 3.3 mL, 106 mmol) was added to a suspension of 2-[([1,3]thiazolo[4,5-c]quinolin-2-yl)methoxy]-1H-isoindole-1,3(2H)-dione (19.2 g, 53.1 mmol) in ethanol (300 mL), and the reaction was stirred at room temperature for 2.5 hours and filtered. The filter cake was washed with ethanol and dried overnight in a vacuum oven to provide 16.2 g of 2-(aminooxy)methyl[1,3]thiazolo[4,5-c]quinoline as a tan solid containing some phthalhydrazide. The filtrate was concentrated under reduced pressure to provide 5.89 g of the same mixture as a yellow solid. Some of the phthalhydrazide was removed from the mixture by recrystallization from ethanol.

Part C

Triethylamine (15.2 mL, 109 mmol) and di-tert-butyl dicarbonate (19.1 g, 87.3 mmol) were added to a mixture of the material from Part B (10.1 g) in THF (300 mL) and water (100 mL), and the reaction was stirred overnight at room temperature. The reaction was incomplete as determined by LC/MS analysis, and additional triethylamine (5 mL) and di-tert-butyl dicarbonate (6 g) were added. The reaction was stirred overnight. The aqueous layer was separated and extracted with THF (2×100 mL), and the combined organic fractions were dried over magnesium sulfate, filtered, and concentrated under reduced pressure. The residue was dissolved in toluene and concentrated three times to provide a yellow oil, which was purified by column chromatography using a HORIZON HPFC system (silica cartridge, eluting with 3 to 10% methanol in dichloromethane) to provide 7.52 g of tert-butyl[1,3]thiazolo[4,5-c]quinolin-2-ylmethoxycarbamate.

Part D

The methods described in Parts A and B of Example 1 were used to oxidize and then aminate tert-butyl[1,3]thiazolo[4,5-c]quinolin-2-ylmethoxycarbamate. The reaction with potassium ethoxide was heated at reflux to drive it to completion. Products from three separate runs were combined to provide tert-butyl(4-amino[1,3]thiazolo[4,5-c]quinolin-2-yl)methoxycarbamate as a brown solid.

Part E

Hydrogen chloride (20 mL of a 4 M solution in 1,4-dioxane) was added to a stirred suspension of tert-butyl(4-amino[1,3]thiazolo[4,5-c]quinolin-2-yl)methoxycarbamate (3.63 g, 10.5 mmol) in dichloromethane (80 mL). The reaction was stirred for 4.5 hours at room temperature and then concentrated under reduced pressure to provide 3.65 g of 2-(aminooxy)methyl[1,3]thiazolo[4,5-c]quinolin-4-amine trihydrochloride as a yellow solid.

Part F

A reagent from the table below (1.1 equivalents, 0.11 mmol) was added to a test tube containing a solution of 2-(aminooxy)methyl[1,3]thiazolo[4,5-c]quinolin-4-amine trihydrochloride (36 mg, 0.10 mmol) and N,N-diisopropylethylamine (87 µL, 0.50 mmol) in N,N-dimethylacetamide (1 mL). Each test tube was capped and placed on a shaker at ambient temperature overnight Two drops of water were added to each test tube, and then the solvent was removed by vacuum centrifugation. The compounds were purified by prep HPLC according to the method described in Examples 4-72. The table below shows the reagent used for each example, the structure of the resulting compound, and the observed accurate mass for the isolated trifluoroacetate salt.

Examples 73-114

| Example | Reagent | R | Measured Mass (M + H) |
|---|---|---|---|
| 73 | None | H | 247.0674 |
| 74 | Propionyl chloride | C(O)CH2CH3 | 303.0941 |
| 75 | Methyl chloroformate | C(O)OCH3 | 305.0730 |
| 76 | Cyclopropanecarbonyl chloride | C(O)-cyclopropyl | 315.0941 |
| 77 | Butryl chloride | C(O)CH2CH2CH3 | 317.1084 |
| 78 | Isobutyryl chloride | C(O)CH(CH3)2 | 317.1095 |
| 79 | Ethyl chloroformate | C(O)OCH2CH3 | 319.0896 |

-continued

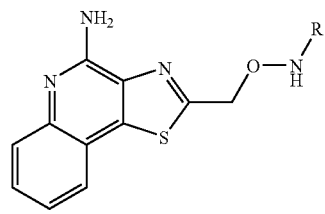

| Example | Reagent | R | Measured Mass (M + H) |
|---|---|---|---|
| 80 | Methoxyacetyl chloride | –C(O)CH$_2$OCH$_3$ | 319.0889 |
| 81 | Cyclobutanecarbonyl chloride | –C(O)-cyclobutyl | 329.1098 |
| 82 | 2-Methylbutyryl chloride | –C(O)CH(CH$_3$)CH$_2$CH$_3$ | 331.1227 |
| 83 | Ivobaleryl chloride | –C(O)CH$_2$CH(CH$_3$)$_2$ | 331.1229 |
| 84 | Pivaloyl chloride | –C(O)C(CH$_3$)$_3$ | 331.1259 |
| 85 | Benzoyl chloride | –C(O)C$_6$H$_5$ | 351.0930 |
| 86 | m-Toluoyl chloride | –C(O)(3-CH$_3$-C$_6$H$_4$) | 365.1057 |
| 87 | o-Toluoyl chloride | –C(O)(2-CH$_3$-C$_6$H$_4$) | 365.1101 |
| 88 | p-Toluoyl chloride | –C(O)(4-CH$_3$-C$_6$H$_4$) | 365.1044 |
| 89 | Phenylacetyl chloride | –C(O)CH$_2$C$_6$H$_5$ | 365.1100 |

-continued

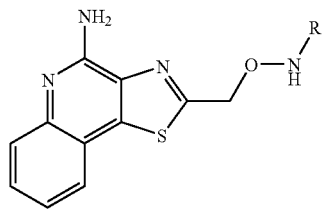

| Example | Reagent | R | Measured Mass (M + H) |
|---|---|---|---|
| 90 | 2-Chlorobenzoyl chloride | 2-chlorobenzoyl | 385.0515 |
| 91 | 3-Chlorobenzoyl chloride | 3-chlorobenzoyl | 385.0562 |
| 92 | Isonicotinoyl chloride hydrochloride | isonicotinoyl | 352.0888 |
| 93 | Nicotinoyl chloride hydrochloride | nicotinoyl | 352.0901 |
| 94 | Picolinyl chloride hydrochloride | picolinoyl | 352.0897 |
| 95 | Methanesulfonyl chloride | methanesulfonyl | 325.0458 |
| 96 | Ethanesulfonyl chloride | ethanesulfonyl | 339.0614 |
| 97 | 1-Propanesulfonyl chloride | 1-propanesulfonyl | 353.0767 |
| 98 | Dimethylsulfamoyl chloride | dimethylsulfamoyl | 354.0699 |
| 99 | 1-Butanesulfonyl chloride | 1-butanesulfonyl | 367.0912 |
| 100 | 1-Methylimidazole-4-sulfonyl chloride | 1-methylimidazole-4-sulfonyl | 391.0687 |

-continued
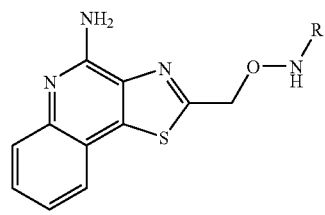
| Example | Reagent | R | Measured Mass (M + H) |
|---|---|---|---|
| 101 | 2,2,2-Trifluoroethanesulfonyl chloride | | 393.0331 |
| 102 | Ethyl isocyanate | | 318.1029 |
| 103 | Isopropyl isocyanate | | 332.1198 |
| 104 | n-Butyl isocyanate | | 346.1313 |
| 105 | sec-Butyl isocyanate | | 346.1350 |
| 106 | Cyclopentyl isocyanate | | 358.1353 |
| 107 | Cyclohexyl isocyanate | | 372.1513 |
| 108 | Benzyl isocyanate | | 380.1190 |
| 109 | m-Tolyl isocyanate | | 380.1198 |

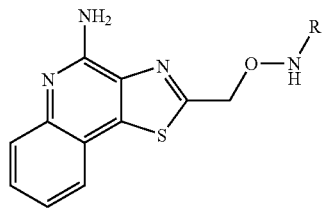

| Example | Reagent | R | Measured Mass (M + H) |
|---|---|---|---|
| 110 | 3-Chlorophenyl isocyanate | *(3-chlorophenyl)carbamoyl group* | 400.0677 |
| 111 | N,N-Dimethylcarbamoyl chloride | *N,N-dimethylcarbamoyl group* | 318.1052 |
| 112 | 4-Morpholinylcarbonyl chloride | *morpholine-4-carbonyl group* | 360.1167 |
| 113 | 4-Methyl-1-piperazinecarbonyl chloride | *4-methylpiperazine-1-carbonyl group* | 373.1470 |
| 114 | N-Methyl-N-phenylcarbamoyl chloride | *N-methyl-N-phenylcarbamoyl group* | 380.1192 |

Examples 115-137

An aldehyde or ketone from the table below (1.1 equivalents. 0.11 mmol) was added to a test tube containing a solution of 2-(aminooxy)methyl-7-[1,3]thiazolo[4,5-c]quinolin-4-amine (prepared in Parts A through H of Example 2, 49 mg, 0.1 mmol) in N,N-dimethylacetamide (1 mL). The test tube was capped and placed on a shaker at room temperature for 2 hours. The solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound Reversed phase prep HPLC was performed with non-linear gradient elution from 5-95% B where A is 0.05% trifluoroacetic acid/ water and B is 0.05% trifluoroacetic add/acetonitrile. Fractions were collected by mass-selective triggering. The table below shows the ketone or aldehyde used for each example, the structure of the resulting compound, and the observed accurate mass for the isolated trifluoroacetate salt. While the structures in the table for R are drawn as the trans isomer, each Example compound may contain cis isomer, may be completely cis isomer, or may be completely trans isomer, as the isomers) present was not determined.

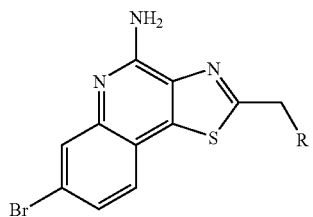

| Example | Reagent | R | Measured Mass (M + H) |
|---|---|---|---|
| 115 | None | —O—NH₂ | 324.9761 |
| 116 | 2-Hydroxyacetaldehyde | —O—N=CH—CH₂OH | 366.9874 |
| 117 | Cyclopropanecarboxaldehyde | —O—N=CH—cyclopropyl | 377.0095 |
| 118 | Butyraldehyde | —O—N=CH—CH₂CH₂CH₃ | 379.0210 |
| 119 | Isovaleraldehyde | —O—N=CH—CH₂CH(CH₃)₂ | 393.0399 |
| 120 | Trimethylacetaldehyde | —O—N=CH—C(CH₃)₃ | 393.0401 |
| 121 | DL-Glyceraldehyde | —O—N=CH—CH(OH)—CH₂OH | 396.9964 |
| 122 | Tetrahydrofuran-3-carboxaldehyde | —O—N=CH—(tetrahydrofuran-3-yl) | 407.0167 |
| 123 | Isonicotinaldehyde | —O—N=CH—(pyridin-4-yl) | 414.0024 |
| 124 | Nicotinaldehyde | —O—N=CH—(pyridin-3-yl) | 414.0048 |

-continued
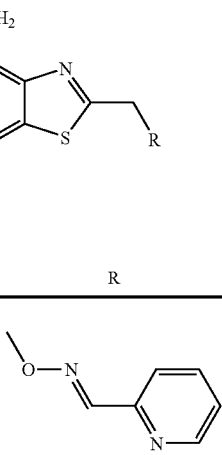
| Example | Reagent | R | Measured Mass (M + H) |
|---|---|---|---|
| 125 | Picolinaldehyde | 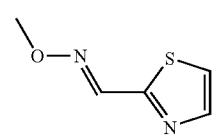 | 414.0028 |
| 126 | 2-Thiazolecarboxaldehyde | 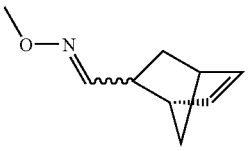 | 419.9623 |
| 124 | 5-Norbornene-2-carboxaldehyde | 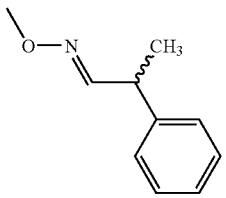 | 429.0392 |
| 128 | 2-Phenylpropionaldehyde | 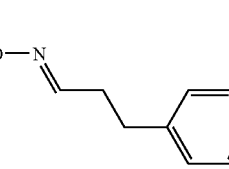 | 441.0396 |
| 129 | 3-Phenylpropionaldehyde | 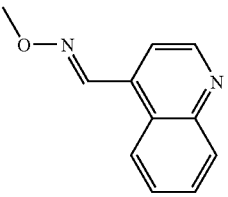 | 441.0403 |
| 130 | 4-Quinolinecarboxaldehyde | 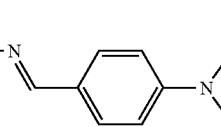 | 464.0159 |
| 131 | 1-(4-Formylphenyl)-1H-imidazole | 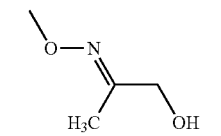 | 479.0286 |
| 132 | Hydroxyacetone |  | 381.0043 |

-continued
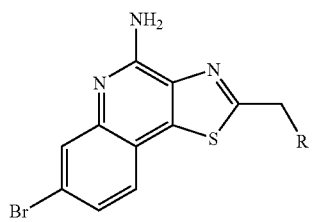
| Example | Reagent | R | Measured Mass (M + H) |
|---|---|---|---|
| 133 | Cyclopentanone | [structure: methoxyimino-cyclopentane] | 391.0208 |
| 134 | 3-Hydroxy-2-butanone | [structure: methoxyimino with CH3 and OH] | 395.0181 |
| 135 | Dihydroxyacetone | [structure: methoxyimino with two CH2OH] | 396.9964 |
| 136 | Cyclohexanone | [structure: methoxyimino-cyclohexane] | 405.0395 |
| 137 | 1-Acetyl-4-piperidone | [structure: methoxyimino-N-acetylpiperidine] | 448.0444 |

Example 138

4-Amino-7-phenyl-thiazolo[4,5-c]quinoline-2-carbaldehyde O-methyl-oxime

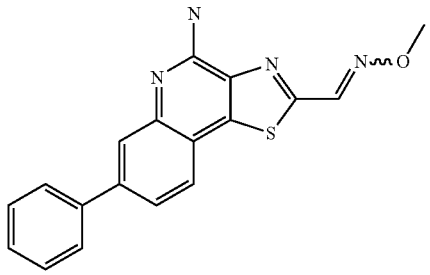 [SMILES: CON=Cc1nc2c(N)nc3cc(-c4ccccc4)ccc3c2s1]

Palladium (D) acetate (0.0014 g, 0.006 mmol) was added to a storing suspension of 4-amino-7-bromo[1,3]thiazolo[4,5-c]quinoline-2-carbaldehyde O-methyloxime (0.700 g, 2.08 mmol), phenylboronic acid (0329 g, 2.70 mmol), triphenylphosphine (0.005 g, 0.019 mmol) and sodium carbonate (0.264 g, 2.49 mmol) in water (4 mL) and 1-propanol (2.5 mL) under a nitrogen atmosphere. The resulting suspension was heated at reflux for 19 hours. The reaction mixture was cooled to ambient temperature, partitioned between brine (25 mL) and dichloromethane (25 mL), and filtered to isolate a solid, which was washed with dichloromethane and water to provide 450 mg of a brown solid. The filtrate was transferred to a separatory funnel and extracted with dichloromethane (3×50 mL). The combined organic fractions were dried over magnesium sulfate, filtered and concentrated under reduced pressure to yield an additional 100 mg of yellow solid. This solid was combined with the solid collected by filtration and purified by column chromatography using a HORIZON HPFC system (silica cartridge, eluting with dichloromethane—10% methanol in dichloromethane). The resulting 252 mg of yellow solid was crystallized from a mixture of hot dichloromethane and ethanol and isolated by filtration to yield 116 mg of 4-amino-7-phenyl-thiazolo[4,5-c]quinoline-2-carbaldehyde O-methyl-oxime as a yellow solid in a 15:1 mixture of isomers, mp 259-261° C. Anal. calcd for $C_{18}H_{14}N_4OS$: C, 64.65; H, 4.22; N, 16.75. Found: C, 64.45; H, 4.29; N, 16.72.

Example 139

N-{3-[4-Amino-2-(methoxyimino-methyl)-thiazolo[4,5-c]quinolin-7-yl]-phenyl}-methanesulfonamide

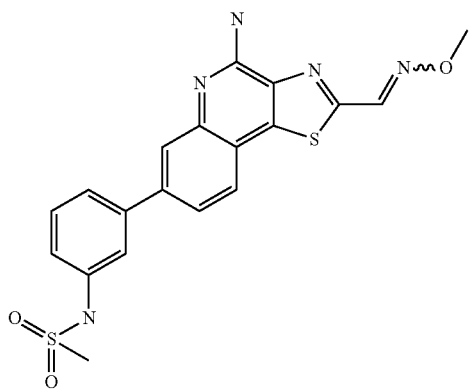 [SMILES: CON=Cc1nc2c(N)nc3cc(-c4cccc(NS(C)(=O)=O)c4)ccc3c2s1]

The method described in Example 138 was followed using 3-(methanesulfonylamino)phenylboronic acid (0.564 g, 2.62 mmol) in lieu of phenylboronic acid. The product was purified by column chromatography using a HORIZON HPFC system (silica cartridge, eluting with 3-7% methanol in dichloromethane) and triturated with methanol to provide 113 mg of N-{3-[4-amino-2-(methoxyimino-methyl)-thiazolo[4,5-c]quinolin-7-yl]-phenyl-methanesulfonamide as a yellow solid, mp 254-256° C., Anal. calcd for $C_{19}H_{17}N_5O_3S_2$: C, 53.38; H, 4.01; N, 16.38. Found: C, 53.17; H, 3.94; N, 16.53.

Exemplary Compounds

Certain exemplary compounds, including some of those described above in the Examples, have the following Formulas (IIc or IId) and the following $R_3$ substituents, wherein each line of the table is matched with Formula IIc or IId to represent a specific embodiment of the invention.

IIc

[Structure: thiazoloquinoline with NH₂, $R_3$, and $CH_2-O-N=C(CH_3)CH_3$ substituent]

IId

[Structure: thiazoloquinoline with NH₂, $R_3$, and $C(H)=N-O-CH_3$ substituent]

| $R_3$ |
| --- |
| hydrogen |
| bromine |
| phenyl |
| 3-(methanesulfonyl)phenyl |
| 3-pyridyl |

Certain exemplary compounds, including some of those described above in the Examples, have the following Formula (IIe) and the following $R_2$ and $R_3$ substituents, wherein each line of the table is matched with Formula IIe to represent a specific embodiment of the invention.

IIe

[Structure: 4-amino thiazolo-quinoline with R2 at thiazole 2-position and R3 at position 7]

| R₂ | R₃ |
|---|---|
| —CH₂—O—NH₂ | hydrogen |
| —CH₂—O—NH—C(O)—CH₃ | hydrogen |
| —CH₂—O—NH—S(O)₂—CH₃ | hydrogen |
| —CH₂—O—NH—C(O)—NH—CH₃ | hydrogen |
| —CH₂—NH—OCH₃ | hydrogen |
| —CH₂—N(CH₃)—OH | hydrogen |
| —CH₂—N(CH₃)—OCH₃ | hydrogen |
| —CH₂—O—NH₂ | bromine |
| —CH₂—O—NH—C(O)—CH₃ | bromine |
| —CH₂—O—NH—S(O)₂—CH₃ | bromine |
| —CH₂—O—NH—C(O)—NH—CH₃ | bromine |
| —CH₂—NH—OCH₃ | bromine |
| —CH₂—N(CH₃)—OH | bromine |
| —CH₂—N(CH₃)—OCH₃ | bromine |
| —CH₂—O—NH₂ | phenyl |
| —CH₂—O—NH—C(O)—CH₃ | phenyl |
| —CH₂—O—NH—S(O)₂—CH₃ | phenyl |
| —CH₂—O—NH—C(O)—NH—CH₃ | phenyl |
| —CH₂—NH—OCH₃ | phenyl |
| —CH₂—N(CH₃)—OH | phenyl |
| —CH₂—N(CH₃)—OCH₃ | phenyl |
| —CH₂—O—NH₂ | 3-(methanesulfonyl)phenyl |
| —CH₂—O—NH—C(O)—CH₃ | 3-(methanesulfonyl)phenyl |
| —CH₂—O—NH—S(O)₂—CH₃ | 3-(methanesulfonyl)phenyl |
| —CH₂—O—NH—C(O)—NH—CH₃ | 3-(methanesulfonyl)phenyl |
| —CH₂—NH—OCH₃ | 3-(methanesulfonyl)phenyl |
| —CH₂—N(CH₃)—OH | 3-(methanesulfonyl)phenyl |
| —CH₂—N(CH₃)—OCH₃ | 3-(methanesulfonyl)phenyl |
| —CH₂—O—NH₂ | 3-pyridyl |
| —CH₂—O—NH—C(O)—CH₃ | 3-pyridyl |
| —CH₂—O—NH—S(O)₂—CH₃ | 3-pyridyl |
| —CH₂—O—NH—C(O)—NH—CH₃ | 3-pyridyl |
| —CH₂—NH—OCH₃ | 3-pyridyl |
| —CH₂—N(CH₃)—OH | 3-pyridyl |
| —CH₂—N(CH₃)—OCH₃ | 3-pyridyl |

Compounds of the invention have been found to modulate cytokine biosynthesis by inducing the production of interferon α and/or tumor necrosis factor α in human cells when tested using one of the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609," *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2\times10^6$ cells/mL. The plates are covered with sterile plastic lids, mixed gently and then incubated for 18 hours to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30° C. to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S.

Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30 μM-0.014 μM) and the DMSO concentration to 0.4%. The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30° C. to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in die assay. A plate-wise scaling factor is calculated for each plate as a ratio of the area of the reference compound on the particular plate to the median expected area for the entire experiment. The data from each plate are men multiplied by the plate-wise scaling factor for all plates. Only data from plates bearing a scaling factor of between 0.5 and 2.0 (for both cytokines IFN-α, TNF-α) are reported. Data from plates with scaling factors outside the above-mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of Formula I:

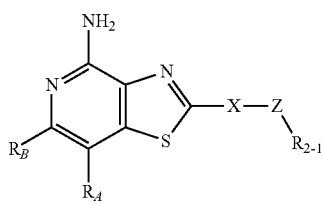

wherein:
Z is selected from the group consisting of:
—O—N=C($R_{2-2}$)—,
—C(=N—O—$R_{2-3}$)—,
—O—N($R_{2-4}$)—Y—, and
—C($R_{2-6}$)(—N(—O$R_{2-3}$)—Y—$R_{2-5}$)—;
X is selected from the group consisting of $C_{1-4}$ alkylene and $C_{3-4}$ alkenylene; with the proviso that X can also be a bond when Z is —C(=N—O—$R_{2-3}$)— or —C($R_{2-6}$)(—N(—O$R_{2-3}$)—Y—$R_{2-5}$)—;
$R_{2-1}$, $R_{2-2}$, $R_{2-3}$, $R_{2-4}$, and $R_{2-5}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$—$R_{2-7}$,
—NH—S(O)$_2$—$R_{2-7}$,
haloalkoxy,
halogen,
cyano,
nitro,
—$N_3$,
heterocyclyl,
aryloxy,
arylalkyleneoxy,
—C(O)—O-alkyl,
—C(O)—N($R_8$)$_2$,
—N($R_8$)—C(O)—$R_{2-7}$,
—NH—C(O)—NH—$R_{2-7}$,
—NH—C(O)—NH$_2$,
—O—(CO)-alkyl, and
—C(O)-alkyl;
with the proviso that $R_{2-3}$ is other than alkenyl wherein the carbon atom bonded to —O— is doubly bonded to another carbon atom;
or $R_{2-1}$ and $R_{2-2}$ can join together to form a ring system selected from the group consisting of:

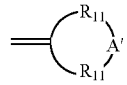

wherein the total number of atoms in the ring is 4 to 9, and

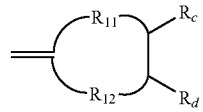

wherein the total number of atoms in the ring is 4 to 9;
or $R_{2-1}$ and $R_{2-4}$ together with the Y group and the nitrogen atom to which they are bonded can join to form a ring selected from the group consisting of:

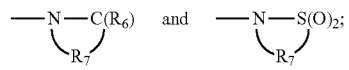

$R_{2-6}$ is selected from the group consisting of hydrogen, $C_{1-4}$alkyl, and phenyl;
$R_{2-7}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —$N_3$;
Y is selected from the group consisting of:
a bond,
—C($R_6$)—,
—S(O)$_2$—,
—S(O)$_2$—N($R_8$)—,

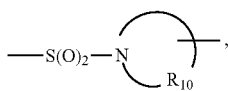

—C(O)—O—,
—C(R₆)—N(R₈)—, and

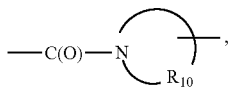

R$_A$ and R$_B$ are each independently selected from the group consisting of:
hydrogen,
alkyl,
alkoxy;
or when taken together, R$_A$ and R$_B$ form a fused benzene ring wherein the fused benzene ring is unsubstituted or substituted by one or more R''' groups;
or when taken together, R$_A$ and R$_B$ form a fused cyclohexene ring, wherein the fused cyclohexene ring is unsubstituted or substituted by one or more R groups;
R is selected from the group consisting of:
halogen,
hydroxy,
alkyl,
alkenyl,
haloalkyl,
alkoxy,
alkylthio, and
—N(R$_9$)$_2$;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R$_6$ is =O;
R$_7$ is C$_{2-7}$ alkylene;
R$_8$ is selected from the group consisting of hydrogen, C$_{1-10}$ alkyl, C$_{2-10}$ alkenyl, C$_{1-10}$ alkoxy-C$_{1-10}$ alkylenyl, hydroxy-C$_{1-10}$ alkylenyl, heteroaryl-C$_{1-10}$ alkylenyl, and aryl-C$_{1-10}$ alkylenyl;
R$_9$ is selected from the group consisting of hydrogen and alkyl;
R$_{10}$ is C$_{3-8}$ alkylene;
R$_{11}$ is C$_{1-6}$ alkylene or C$_{2-6}$ alkenylene, wherein the alkylene or alkenylene is optionally interrupted by one heteroatom;
R$_{12}$ is selected from the group consisting of a bond, C$_{1-5}$ alkylene, and C$_{2-5}$ alkenylene, wherein the alkylene or alkenylene is optionally interrupted by one heteroatom;

R$_c$ and R$_d$ are independently selected from the group consisting of hydrogen; or R$_c$ and R$_d$ can join to form a fused aryl ring or fused 5-10 membered heteroaryl ring containing one to four heteroatoms;
A' is selected from the group consisting of —O—, —S(O)$_{0-2}$—, —N(-Q-R$_4$)—, and —CH$_2$—;
Q is selected from the group consisting of a bond, —C(R$_6$)—, —S(O)$_2$—, —S(O)$_2$—N(R$_8$)—, —C(R$_6$)—O—, and —C(R$_6$)—N(OR$_9$)—;
W is selected from the group consisting of a bond, —C(O)—, and —S(O)$_2$—; and
wherein the one or more R''' groups are one R$_3$ group, or one R$_3$ group and one R group, or one, two, three, or four R groups when on the fused benzene ring; wherein R$_3$ is selected from the group consisting of:
—Z'—R$_4$,
—Z'—X'—R$_4$,
—Z'—X'—Y'—R$_4$, and
X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;
Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q—,
—C(R$_6$)—N(R$_8$)—,
—O—C(R$_6$)—N(R$_8$)—,
—C(R$_6$)—N(OR$_9$)—
—O—N(R$_8$)-Q-,
—O—N=C(R$_4$)—,
—C(=N—O—R$_8$)—,
—CH(—N(—O—R$_8$)-Q—R$_4$)—,

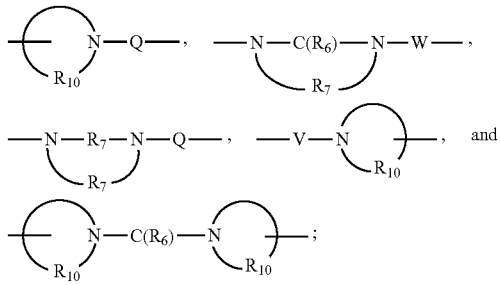

Z' is a bond or —O—;
R$_5$ is selected from the group consisting of:

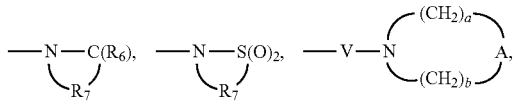

-continued

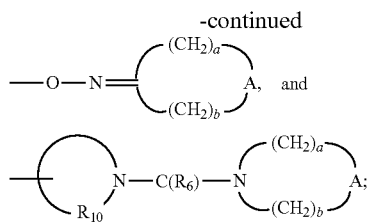

A is selected from the group consisting of —O—, —C(O)—, —S(O)$_{0-2}$—, —CH$_2$—, and —N(-Q-R$_4$)—;
V is selected from the group consisting of —C(R$_6$)—, —O—C(R$_6$)—, —N(R$_8$)—C(R$_6$)—, and —S(O)$_2$; and
a and b are independently integers from 1 to 6 with the proviso that a+b is ≦7;
or a pharmaceutically acceptable salt thereof.

2. A compound of Formula II:

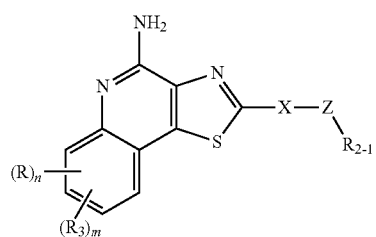

II wherein:
Z is selected from the group consisting of:
—O—N=C(R$_{2-2}$)—,
—C(=N—O—R$_{2-3}$)—,
—O—N(R$_{2-4}$)—Y—, and
—C(R$_{2-6}$)(—N(—OR$_{2-3}$)—Y—R$_{2-5}$)—;
X is selected from the group consisting of C$_{1-4}$ alkylene and C$_{3-4}$ alkenylene; with the proviso that X can also be a bond when Z is —C(=N—O—R$_{2-3}$)— or —C(R$_{2-6}$)(—N(—OR$_{2-3}$)—Y—R$_{2-5}$)—;
R$_{2-1}$, R$_{2-2}$, R$_{2-3}$, R$_{2-4}$, and R$_{2-5}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$—R$_{2-7}$,
—NH—S(O)$_2$—R$_{2-7}$,
haloalkoxy,
halogen,
cyano,
nitro,
—N$_3$,
heterocyclyl,
aryloxy,
arylalkyleneoxy,
—C(O)—O-alkyl,
—C(O)—N(R$_8$)$_2$,
—N(R$_8$)—C(O)—R$_{2-7}$,
—NH—C(O)—NH—R$_{2-7}$,
—NH—C(O)—NH$_2$,
—O—(CO)-alkyl, and
—C(O)-alkyl;
with the proviso that R$_{2-3}$ is other than alkenyl wherein the carbon atom bonded to —O— is doubly bonded to another carbon atom;
or R$_{2-1}$ and R$_{2-2}$ can join together to form a ring system selected from the group consisting of:

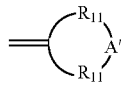

wherein the total number of atoms in the ring is 4 to 9, and

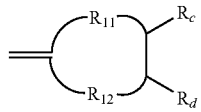

wherein the total number of atoms in the ring is 4 to 9;
or R$_{2-1}$ and R$_{2-4}$ together with the Y group and the nitrogen atom to which they are bonded can join to form a ring selected from the group consisting of:

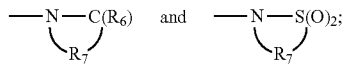

R$_{2-6}$ is selected from the group consisting of hydrogen, C$_{1-4}$alkyl, and phenyl;
R$_{2-7}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N$_3$;
Y is selected from the group consisting of a bond, —C(R$_6$)—, —S(O)$_2$—, —S(O)$_2$—N(R$_8$)—,

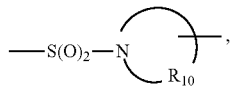

—C(O)—O—, —C($R_6$)—N($R_8$)—, and

—C(O)—N⟨ring with $R_{10}$⟩ ,

;

R is selected from the group consisting of:
  halogen,
  hydroxy,
  alkyl,
  alkenyl,
  haloalkyl,
  alkoxy,
  alkylthio, and
  —N($R_9$)$_2$;
$R_3$ is selected from the group consisting of:
  —Z'—$R_4$,
  —Z'—X'—$R_4$,
  —Z'—X'—Y'—$R_4$,
  and
  —Z'—X'—$R_5$;
n is an integer from 0 to 4;
m is 0 or 1; with the proviso that when m is 1, then n is 0 or 1;
X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;
Y' is selected from the group consisting of —O—, —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—, —O—N($R_8$)-Q-, —O—N=C($R_4$)—, —C(=N—O—$R_8$)—, —CH(—N(—O—$R_8$)-Q-$R_4$)—, ⟨ring with $R_{10}$⟩N—Q—,  —N—C($R_6$)—N—W—
                                    $R_7$ —N—$R_7$—N—Q—,  —V—N⟨ring with $R_{10}$⟩, and
    $R_7$ ⟨ring with $R_{10}$⟩N—C($R_6$)—N⟨ring with $R_{10}$⟩ ;

Z' is a bond or —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

—N—C($R_6$),  —N—S(O)$_2$,  —V—N⟨(CH$_2$)$_a$ / (CH$_2$)$_b$⟩A,
   $R_7$         $R_7$

—O—N=⟨(CH$_2$)$_a$ / (CH$_2$)$_b$⟩A',  and

⟨ring with $R_{10}$⟩N—C($R_6$)—N⟨(CH$_2$)$_a$ / (CH$_2$)$_b$⟩A;

$R_6$ is =O;
$R_7$ is $C_{2-7}$ alkylene;
$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;
$R_9$ is selected from the group consisting of hydrogen and alkyl;
$R_{10}$ is $C_{3-8}$ alkylene;
$R_{11}$ is $C_{1-6}$ alkylene or $C_{2-6}$ alkenylene, wherein the alkylene or alkenylene is optionally interrupted by one heteroatom;
$R_{12}$ is selected from the group consisting of a bond, $C_{1-5}$ alkylene, and $C_{2-5}$ alkenylene, wherein the alkylene or alkenylene is optionally interrupted by one heteroatom;
$R_c$ and $R_d$ are independently selected from the group consisting of hydrogen; or $R_c$ and $R_d$ can join to form a fused aryl ring or fused 5-10 membered heteroaryl ring containing one to four heteroatoms;
A is selected from the group consisting of —O—, —C(O)—, —S(O)$_{0-2}$—, —CH$_2$—, and —N(-Q-$R_4$)—;
A' is selected from the group consisting of —O—, —S(O)$_{0-2}$—, —N(-Q-$R_4$)—, and —CH$_2$—;
Q is selected from the group consisting of a bond, —C($R_6$)—, —S(O)$_2$—, —S(O)$_2$—N($R_8$)—, —C($R_6$)—O—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

3. The compound or salt of claim 1 wherein R is halogen or hydroxy.

4. The compound or salt of claim 2 wherein n is 0.

5. The compound or salt of claim 2 wherein $R_3$ is selected from the group consisting of phenyl, pyridin-3-yl, pyridin-4-yl, 5-(hydroxymethyl)pyridin-3-yl, 2-ethoxyphenyl, 3-(morpholine-4-carbonyl)phenyl, and 3-(N,N-dimethylaminocarbonyl)phenyl.

6. The compound or salt of claim 2 wherein m is 0.

7. The compound or salt of claim 1 wherein Z is —O—N=C($R_{2-2}$)—.

8. The compound or salt of claim 7 wherein $R_{2-1}$ and $R_{2-2}$ join together to form a ring system selected from the group consisting of

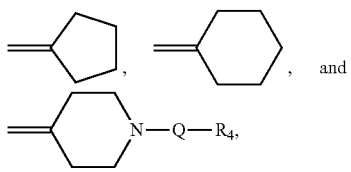

wherein Q is a bond or —C(O)—, and $R_4$ is alkyl.

9. The compound or salt of claim 7 wherein at least one of $R_{2-1}$ or $R_{2-2}$ is selected from the group consisting of alkyl, alkenyl, aryl, arylalkylenyl, heteroaryl, heteroarylalkylenyl, heterocyclyl, and heterocyclylalkylenyl, each of which is unsubstituted or substituted by one or more substituents selected from the group consisting of hydroxy, alkyl, haloalkyl, hydroxyalkyl, alkoxy, dialkylamino, —S(O)$_{0-2}$—$R_{2-7}$, —NH—S(O)$_2$—$R_{2-7}$, haloalkoxy, halogen, cyano, nitro, heterocyclyl, aryloxy, arylalkyleneoxy, —C(O)—O-alkyl, —C(O)—N($R_8$)$_2$, —N($R_8$)—C(O)—$R_{2-7}$, —N(H)—C(O)—NH—$R_{2-7}$, —O—(CO)-alkyl, and —C(O)-alkyl.

10. The compound or salt of claim 9 wherein at least one of $R_{2-1}$ or $R_{2-2}$ is selected from the group consisting of alkyl, aryl, arylalkylenyl, heteroaryl, and heterocyclyl, each of which is unsubstituted or substituted by one or more substituents selected from the group consisting of hydroxy, alkyl, alkoxy, halogen, cyano, and —C(O)—O-alkyl.

11. The compound or salt of claim 10 wherein $R_{2-1}$ and $R_{2-2}$ are independently $C_{1-10}$ alkyl.

12. The compound or salt of claim 11 wherein $R_{2-1}$ and $R_{2-2}$ are each methyl.

13. The compound or salt of claim 7 wherein one of $R_{2-1}$ or $R_{2-2}$ is hydrogen.

14. The compound or salt of claim 1 wherein Z is —O—N($R_{2-4}$)—Y—.

15. The compound or salt of claim 14 wherein $R_{2-4}$ is hydrogen.

16. The compound or salt of claim 14 wherein Y is selected from the group consisting of —C(O)—, —S(O)$_2$—, —S(O)$_2$—N($R_8$)—, —C(O)—O—, and —C(O)—N($R_8$)—.

17. The compound or salt of claim 14 wherein $R_{2-1}$ is selected from the group consisting of alkyl, aryl, arylalkylenyl, heteroaryl, and heterocyclyl, each of which is unsubstituted or substituted with one or more substituents selected from the group consisting of alkyl, alkoxy, and halogen.

18. The compound or salt of claim 1 wherein Z is —C(=N—O—$R_{2-3}$)—.

19. The compound or salt of claim 18 wherein $R_{2-3}$ is selected from the group consisting of hydrogen, alkyl, arylalkylenyl, and heteroarylalkylenyl.

20. The compound or salt of claim 19 wherein $R_{2-3}$ is hydrogen, $C_{1-4}$ alkyl, benzyl, or pyridin-2-ylmethyl.

21. The compound or salt of claim 1 wherein Z is —C($R_{2-6}$)(—N(—O$R_{2-3}$)—Y—$R_{2-5}$)—.

22. The compound or salt of claim 21 wherein $R_{2-6}$ is hydrogen.

23. The compound or salt of claim 21 wherein $R_{2-3}$ is selected from the group consisting of hydrogen, alkyl, arylalkylenyl, and heteroarylalkylenyl.

24. The compound or salt of claim 23 wherein $R_{2-3}$ is hydrogen, $C_{1-4}$ alkyl, benzyl, or pyridin-2-ylmethyl.

25. The compound or salt of claim 21 wherein $R_{2-5}$ is hydrogen or methyl, and Y is a bond.

26. The compound or salt of claim 18 wherein $R_{2-1}$ is selected from the group consisting of hydrogen, alkyl, and aryl.

27. The compound or salt of claim 26 wherein $R_{2-1}$ is hydrogen, $C_{1-4}$ alkyl, or phenyl.

28. The compound or salt of claim 1 wherein X is $C_{1-4}$ alkylene.

29. The compound or salt of claim 28 wherein X is methylene.

30. The compound or salt of claim 18 wherein X is a bond.

31. A pharmaceutical composition comprising a therapeutically effective amount of a compound or salt of claim 1 and a pharmaceutically acceptable carrier.

32. A method of inducing cytokine biosynthesis in an animal comprising administering an effective amount of a compound or salt of claim 1 to the animal.

* * * * *